(12) United States Patent
Oron et al.

(10) Patent No.: US 11,648,410 B2
(45) Date of Patent: *May 16, 2023

(54) WIRELESS NEUROSTIMULATORS

(71) Applicant: BLUEWIND MEDICAL LTD., Herzliya (IL)

(72) Inventors: Gur Oron, Tel Aviv (IL); Yossi Gross, Moshav Mazor (IL); Danny Neeman, Ramat Hasharon (IL); Shlomo Ronen, Raanana (IL)

(73) Assignee: BLUEWIND MEDICAL LTD., Herzliya (IL)

( * ) Notice: Subject to any disclaimer, the term of this patent is extended or adjusted under 35 U.S.C. 154(b) by 458 days.

This patent is subject to a terminal disclaimer.

(21) Appl. No.: 16/863,153

(22) Filed: Apr. 30, 2020

(65) Prior Publication Data

US 2020/0254266 A1 Aug. 13, 2020

Related U.S. Application Data

(63) Continuation of application No. 15/638,924, filed on Jun. 30, 2017, now Pat. No. 10,653,888, which is a
(Continued)

(51) Int. Cl.
*A61N 1/378* (2006.01)
*A61N 1/375* (2006.01)
(Continued)

(52) U.S. Cl.
CPC ....... *A61N 1/3787* (2013.01); *A61N 1/36139* (2013.01); *A61N 1/375* (2013.01);
(Continued)

(58) Field of Classification Search
CPC .............. A61N 1/3787; A61N 1/36139; A61N 1/37205; A61N 1/375; A61N 1/0556;
(Continued)

(56) References Cited

U.S. PATENT DOCUMENTS

3,411,507 A 11/1968 Wingrove
3,693,625 A 9/1972 Auphan
(Continued)

FOREIGN PATENT DOCUMENTS

CN 101048194 10/2007
CN 101500643 8/2009
(Continued)

OTHER PUBLICATIONS

U.S. Appl. No. 15/638,924, filed Jun. 30, 2017, published as 2017/0296426, issued as U.S. Pat. No. 10,653,888.
(Continued)

*Primary Examiner* — Pamela M. Bays
(74) *Attorney, Agent, or Firm* — Sughrue Mion, PLLC

(57) ABSTRACT

A neurostimulator implant includes an insulating member and an elongate circuitry unit. The circuitry unit includes (a) a first electrode, disposed on an outer surface of a first end portion of the circuitry unit; (b) a second electrode, disposed on an outer surface of a second end portion of the circuitry unit; and (c) circuitry, disposed inside the circuitry unit, and configured to be wirelessly powered to drive an electrical current between the first and second electrodes. The circuitry unit is disposed alongside a medial part of the insulating member, bulging away from the insulating member to define a generally arced portion of the implant. Lateral parts of the insulating member extend laterally outward from the medial part to define lateral zones laterally beyond the circuitry unit. The second side of the insulating member defines a generally flat side of the implant. Other embodiments are also described.

21 Claims, 14 Drawing Sheets

Related U.S. Application Data continuation of application No. 14/374,375, filed as application No. PCT/IL2013/050069 on Jan. 24, 2013, now abandoned.

(60) Provisional application No. 61/662,073, filed on Jun. 20, 2012, provisional application No. 61/591,024, filed on Jan. 26, 2012.

(51) Int. Cl.

| | | |
|---|---|---|
| *A61N 1/372* | (2006.01) | |
| *A61N 1/36* | (2006.01) | |
| A61N 5/02 | (2006.01) | |
| A61N 5/04 | (2006.01) | |
| A61H 23/00 | (2006.01) | |
| A61N 1/05 | (2006.01) | |

(52) U.S. Cl.
CPC .......... *A61N 1/37205* (2013.01); *A61H 23/00* (2013.01); *A61N 1/0556* (2013.01); *A61N 1/36067* (2013.01); *A61N 1/36071* (2013.01); *A61N 1/36167* (2013.01); *A61N 1/3756* (2013.01); *A61N 1/37288* (2013.01); *A61N 5/022* (2013.01); *A61N 5/04* (2013.01)

(58) Field of Classification Search
CPC ............ A61N 1/36067; A61N 1/36071; A61N 1/37288; A61N 1/3756
See application file for complete search history.

(56) References Cited

U.S. PATENT DOCUMENTS

| | | |
|---|---|---|
| 3,727,616 A | 4/1973 | Lenzkes |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,036,854 A | 8/1991 | Schollmeyer et al. |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,344,439 A | 9/1994 | Otten |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr. |
| 5,509,924 A | 4/1996 | Paspa et al. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,071,274 A | 6/2000 | Thompson et al. |
| 6,091,992 A | 6/2000 | Bourgeois |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,496,729 B2 | 12/2002 | Thompson |
| 6,496,730 B1 | 12/2002 | Kleckner et al. |
| 6,582,441 B1 | 6/2003 | He et al. |
| 6,591,139 B2 | 7/2003 | Loftin et al. |

(56) References Cited

U.S. PATENT DOCUMENTS

| | | |
|---|---|---|
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,712,772 B2 | 3/2004 | Cohen et al. |
| 6,721,603 B2 | 4/2004 | Zabara et al. |
| 6,735,474 B1 * | 5/2004 | Loeb ............... A61N 1/36007 607/41 |
| 6,735,475 B1 | 5/2004 | Whitehurst et al. |
| 6,770,022 B2 | 8/2004 | Mechlenburg |
| 6,788,973 B2 | 9/2004 | Davis et al. |
| 6,788,975 B1 | 9/2004 | Whitehurst et al. |
| 6,804,561 B2 | 10/2004 | Stover |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 6,950,706 B2 | 9/2005 | Rodriguez et al. |
| 6,993,384 B2 | 1/2006 | Bradley et al. |
| 7,015,769 B2 | 3/2006 | Schulman et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,689 B1 | 5/2006 | Whitehurst et al. |
| 7,054,692 B1 | 5/2006 | Whitehurst et al. |
| 7,110,820 B2 | 9/2006 | Tcheng et al. |
| 7,149,575 B2 | 12/2006 | Ostroff et al. |
| 7,151,914 B2 | 12/2006 | Brewer |
| 7,174,218 B1 | 2/2007 | Kuzma |
| 7,177,690 B2 | 2/2007 | Woods et al. |
| 7,177,698 B2 | 2/2007 | Klosterman et al. |
| 7,190,998 B2 | 3/2007 | Shalev et al. |
| 7,203,549 B2 | 4/2007 | Schommer et al. |
| 7,209,792 B1 | 4/2007 | Parramon et al. |
| 7,212,867 B2 | 5/2007 | Venrooij et al. |
| 7,216,000 B2 | 5/2007 | Sieracki et al. |
| 7,225,032 B2 | 5/2007 | Schmeling et al. |
| 7,228,178 B2 | 6/2007 | Carroll |
| 7,239,921 B2 | 7/2007 | Canfield et al. |
| 7,242,982 B2 | 7/2007 | Singhal et al. |
| 7,254,449 B2 | 8/2007 | Karunasiri |
| 7,263,402 B2 | 8/2007 | Thacker et al. |
| 7,277,748 B2 | 10/2007 | Wingeier et al. |
| 7,277,749 B2 | 10/2007 | Gordon et al. |
| 7,286,880 B2 | 10/2007 | Olson et al. |
| 7,286,881 B2 | 10/2007 | Schommer et al. |
| 7,289,853 B1 | 10/2007 | Campbell et al. |
| 7,292,890 B2 | 11/2007 | Whitehurst et al. |
| 7,308,316 B2 | 12/2007 | Schommer |
| 7,324,852 B2 | 1/2008 | Barolat et al. |
| 7,324,853 B2 | 1/2008 | Ayal |
| 7,330,756 B2 | 2/2008 | Marnfeldt |
| 7,337,007 B2 | 2/2008 | Nathan et al. |
| 7,342,508 B2 | 3/2008 | Morgan et al. |
| 7,363,087 B2 | 4/2008 | Nghiem et al. |
| 7,376,466 B2 | 5/2008 | He et al. |
| 7,389,145 B2 | 6/2008 | Kilgore et al. |
| 7,483,748 B2 | 1/2009 | Torgerson et al. |
| 7,483,752 B2 | 1/2009 | Von arx et al. |
| 7,489,561 B2 | 2/2009 | Armstrong et al. |
| 7,502,652 B2 | 3/2009 | Gaunt et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,536,226 B2 | 5/2009 | Williams |
| 7,539,538 B2 | 5/2009 | Parramon et al. |
| 7,561,921 B2 | 7/2009 | Phillips et al. |
| 7,565,204 B2 | 7/2009 | Matei |
| 7,628,750 B2 | 12/2009 | Cohen |
| 7,630,771 B2 | 12/2009 | Cauller |
| 7,634,313 B1 | 12/2009 | Kroll et al. |
| 7,643,147 B2 | 1/2010 | Pless |
| 7,647,117 B2 | 1/2010 | Bauhahn |
| 7,650,192 B2 | 1/2010 | Wahlstrand |
| 7,655,014 B2 | 2/2010 | Ko et al. |
| 7,657,311 B2 | 2/2010 | Bardy et al. |
| 7,657,317 B2 | 2/2010 | Thacker et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,680,540 B2 | 3/2010 | Jensen et al. |
| 7,711,434 B2 | 5/2010 | Denker et al. |
| 7,736,379 B2 | 6/2010 | Ewers et al. |
| 7,747,325 B2 | 6/2010 | Dilorenzo |
| 7,780,625 B2 | 8/2010 | Bardy |
| 7,797,050 B2 | 9/2010 | Libbus et al. |
| 7,801,602 B2 | 9/2010 | McClure et al. |
| 7,803,142 B2 | 9/2010 | Longson et al. |
| 7,809,437 B2 | 10/2010 | Palmer et al. |
| 7,817,280 B2 | 10/2010 | Pless |
| 7,822,480 B2 | 10/2010 | Park et al. |
| 7,848,818 B2 | 12/2010 | Barolat et al. |
| 7,869,867 B2 | 1/2011 | Armstrong et al. |
| 7,894,905 B2 | 2/2011 | Pless et al. |
| 7,899,547 B1 | 3/2011 | Emadi et al. |
| 7,899,556 B2 | 3/2011 | Nathan et al. |
| 7,904,171 B2 | 3/2011 | Parramon et al. |
| 7,912,551 B2 | 3/2011 | Wosmek |
| 7,925,350 B1 | 4/2011 | Palmer |
| 7,917,226 B2 | 5/2011 | Nghiem |
| 7,937,148 B2 | 5/2011 | Jacobson |
| 7,941,218 B2 | 5/2011 | Sambelashvili et al. |
| 7,962,211 B2 | 6/2011 | Torgerson et al. |
| 7,962,220 B2 | 6/2011 | Kolafa et al. |
| 7,974,706 B2 | 7/2011 | Moffitt et al. |
| 7,979,126 B2 | 7/2011 | Payne et al. |
| 7,991,467 B2 | 8/2011 | Markowitz et al. |
| 7,996,079 B2 | 8/2011 | Armstrong |
| 7,996,089 B2 | 8/2011 | Haugland et al. |
| 7,996,092 B2 | 8/2011 | Mrva et al. |
| 8,005,547 B2 | 8/2011 | Forsberg et al. |
| 8,019,443 B2 | 9/2011 | Scheicher et al. |
| 8,050,771 B2 | 11/2011 | Yamamoto et al. |
| 8,055,336 B1 | 11/2011 | Schulman et al. |
| 8,055,350 B2 | 11/2011 | Roberts |
| 8,075,556 B2 | 12/2011 | Betts |
| 8,086,313 B2 | 12/2011 | Singhal et al. |
| 8,090,438 B2 | 1/2012 | Bardy et al. |
| 8,115,448 B2 | 2/2012 | John |
| 8,127,424 B2 | 3/2012 | Haller et al. |
| 8,131,377 B2 | 3/2012 | Shhi et al. |
| 8,140,168 B2 | 3/2012 | Olson et al. |
| 8,170,675 B2 | 5/2012 | Alataris et al. |
| 8,170,681 B2 | 5/2012 | Jimenez et al. |
| 8,175,719 B2 | 5/2012 | Shi et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,229,567 B2 | 7/2012 | Phillips et al. |
| 8,244,367 B2 | 8/2012 | Wahlstrand et al. |
| 8,255,057 B2 | 8/2012 | Fang et al. |
| 8,260,432 B2 | 9/2012 | DiGiore et al. |
| 8,265,770 B2 | 9/2012 | Toy et al. |
| 8,306,627 B2 | 11/2012 | Armstrong |
| 8,311,638 B2 | 11/2012 | Aghassian |
| 8,321,028 B1 | 11/2012 | Thenuwara et al. |
| 8,335,569 B2 | 12/2012 | Aghassian |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,267 B2 | 1/2013 | Schleicher et al. |
| 8,369,963 B2 | 2/2013 | Parramon et al. |
| 8,374,700 B2 | 2/2013 | Haubrich et al. |
| 8,386,047 B2 | 2/2013 | Koester |
| 8,386,048 B2 | 2/2013 | McClure et al. |
| 8,396,559 B2 | 3/2013 | Alataris et al. |
| 8,428,731 B2 | 4/2013 | Armstrong |
| 8,428,744 B2 | 4/2013 | Stancer et al. |
| 8,428,746 B2 | 4/2013 | DiGiore et al. |

(56) References Cited

U.S. PATENT DOCUMENTS

| | | |
|---|---|---|
| 8,428,748 B2 | 4/2013 | Alataris et al. |
| 8,437,846 B2 | 5/2013 | Swoyer et al. |
| 8,437,853 B2 | 5/2013 | Inman et al. |
| 8,457,744 B2 | 6/2013 | Janzig et al. |
| 8,457,759 B2 | 6/2013 | Parker et al. |
| 8,463,404 B2 | 6/2013 | Levi et al. |
| 8,473,066 B2 | 6/2013 | Aghassian et al. |
| 8,478,420 B2 | 7/2013 | Armstrong et al. |
| 8,483,838 B2 | 7/2013 | Nghiem et al. |
| 8,483,845 B2 | 7/2013 | Sage |
| 8,494,640 B2 | 7/2013 | Peterson et al. |
| 8,494,650 B2 | 7/2013 | Glukhovsky et al. |
| 8,497,804 B2 | 7/2013 | Haubrich et al. |
| 8,498,716 B2 | 7/2013 | Chen et al. |
| 8,509,905 B2 | 8/2013 | Alataris et al. |
| 8,509,906 B2 | 8/2013 | Walker et al. |
| 8,515,558 B1 | 8/2013 | Zweber et al. |
| 8,538,548 B2 | 9/2013 | Shi et al. |
| 8,543,200 B2 | 9/2013 | Lane et al. |
| 8,554,326 B2 | 10/2013 | Alataris et al. |
| 8,555,894 B2 | 10/2013 | Schulman et al. |
| 8,571,651 B2 | 10/2013 | Ben-ezra et al. |
| 8,577,474 B2 | 11/2013 | Rahman et al. |
| 8,588,933 B2 | 11/2013 | Floyd et al. |
| 8,612,014 B2 | 12/2013 | Rahman et al. |
| 8,612,019 B2 | 12/2013 | Moffitt |
| 8,620,435 B2 | 12/2013 | Rooney et al. |
| 8,620,449 B2 | 12/2013 | Zhao et al. |
| 8,626,310 B2 | 1/2014 | Barror et al. |
| 8,634,927 B2 | 1/2014 | Olson et al. |
| 8,644,947 B2 | 2/2014 | Zhu et al. |
| 8,644,948 B2 | 2/2014 | Grevious et al. |
| 8,649,874 B2 | 2/2014 | Alataris et al. |
| 8,660,655 B2 | 2/2014 | Peterson et al. |
| 8,666,491 B2 | 3/2014 | Chen et al. |
| 8,666,504 B2 | 3/2014 | Dronov et al. |
| 8,676,337 B2 | 3/2014 | Kallmyer |
| 8,676,341 B2 | 3/2014 | Kane et al. |
| 8,688,232 B2 | 4/2014 | Finley et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,780 B2 | 5/2014 | Lee |
| 8,718,781 B2 | 5/2014 | Alataris et al. |
| 8,718,782 B2 | 5/2014 | Alataris et al. |
| 8,738,145 B2 | 5/2014 | Goetz et al. |
| 8,750,985 B2 | 6/2014 | Parramon et al. |
| 8,751,009 B2 | 6/2014 | Wacnik |
| 8,755,893 B2 | 6/2014 | Gross et al. |
| 8,761,895 B2 | 6/2014 | Stevenson et al. |
| 8,768,472 B2 | 7/2014 | Fang et al. |
| 8,774,912 B2 | 7/2014 | Gerber |
| 8,774,926 B2 | 7/2014 | Alataris et al. |
| 8,788,045 B2 | 7/2014 | Gross et al. |
| 8,792,988 B2 | 7/2014 | Alataris et al. |
| 8,798,773 B2 | 8/2014 | Mashiach |
| 8,805,519 B2 | 8/2014 | Parker et al. |
| 8,812,135 B2 | 8/2014 | Mashiach |
| 8,843,203 B2 | 9/2014 | Lee et al. |
| 8,849,410 B2 | 9/2014 | Walker et al. |
| 8,849,412 B2 | 9/2014 | Perryman et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,219 B2 | 10/2014 | Trier et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,884,779 B2 | 11/2014 | Herman et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,892,214 B2 | 11/2014 | Bonde et al. |
| 8,903,497 B2 | 12/2014 | Norgaard et al. |
| 8,903,499 B2 | 12/2014 | Pless et al. |
| 8,918,179 B2 | 12/2014 | Peterson et al. |
| 8,918,180 B2 | 12/2014 | Peterson |
| 8,923,988 B2 | 12/2014 | Bradley |
| 8,942,808 B2 | 1/2015 | Peterson et al. |
| 8,954,165 B2 | 2/2015 | Sharma et al. |
| 8,958,884 B2 | 2/2015 | Kothandaraman et al. |
| 8,958,891 B2 | 2/2015 | Kane et al. |
| 8,983,615 B2 | 3/2015 | Tahmasian et al. |
| 8,983,618 B2 | 3/2015 | Yamamoto et al. |
| 8,989,864 B2 | 3/2015 | Funderburk et al. |
| 8,989,868 B2 | 3/2015 | Mashiach et al. |
| 8,994,325 B2 | 3/2015 | Carbunaru et al. |
| 8,996,115 B2 | 3/2015 | Trier et al. |
| 9,002,445 B2 | 4/2015 | Chen |
| 9,002,460 B2 | 4/2015 | Parker |
| 9,002,461 B2 | 4/2015 | Walker et al. |
| 9,002,466 B2 | 4/2015 | Trier et al. |
| 9,020,599 B2 | 4/2015 | Rooney et al. |
| 9,020,602 B2 | 4/2015 | Aghassian |
| 9,026,227 B2 | 5/2015 | Daglow |
| 9,030,159 B2 | 5/2015 | Chen et al. |
| 9,031,666 B2 | 5/2015 | Fell |
| 9,037,261 B2 | 5/2015 | Bradley |
| 9,042,997 B2 | 5/2015 | Rahman et al. |
| 9,044,616 B2 | 6/2015 | Chen et al. |
| 9,056,206 B2 | 6/2015 | Torgerson et al. |
| 9,061,140 B2 | 6/2015 | Shi et al. |
| 9,061,151 B2 | 6/2015 | Mashiach et al. |
| 9,061,159 B2 | 6/2015 | Rahman |
| 9,061,162 B2 | 6/2015 | Mashiach et al. |
| 9,067,072 B2 | 6/2015 | Tahmasian et al. |
| 9,070,507 B2 | 6/2015 | Dronov et al. |
| 9,072,896 B2 | 7/2015 | Dar et al. |
| 9,079,041 B2 | 7/2015 | Park et al. |
| 9,084,900 B2 | 7/2015 | Hershey et al. |
| 9,089,712 B2 | 7/2015 | Joshi et al. |
| 9,095,726 B2 | 8/2015 | Parramon et al. |
| 9,101,774 B2 | 8/2015 | Mashiach et al. |
| 9,119,969 B2 | 9/2015 | Vansickle |
| 9,142,989 B2 | 9/2015 | Fell et al. |
| 9,149,635 B2 | 10/2015 | Denison et al. |
| 9,149,643 B2 | 10/2015 | Tahmasian et al. |
| 9,154,219 B2 | 10/2015 | Polefko et al. |
| 9,155,899 B2 | 10/2015 | Mashiach et al. |
| 9,155,901 B2 | 10/2015 | Dearden et al. |
| 9,162,068 B2 | 10/2015 | Dronov |
| 9,174,051 B2 | 11/2015 | Marnfeldt et al. |
| 9,174,053 B2 | 11/2015 | Zhu |
| 9,186,504 B2 | 11/2015 | Gross |
| 9,192,770 B2 | 11/2015 | Wang et al. |
| 9,199,083 B2 | 12/2015 | Caparso et al. |
| 9,205,258 B2 | 12/2015 | Simon et al. |
| 9,211,418 B2 | 12/2015 | Aghassian |
| 9,216,297 B2 | 12/2015 | Kast et al. |
| 9,220,907 B2 | 12/2015 | Mashiach et al. |
| 9,220,909 B2 | 12/2015 | Carbunaru et al. |
| 9,220,910 B2 | 12/2015 | Colborn |
| 9,225,194 B2 | 12/2015 | Joshi |
| 9,227,075 B2 | 1/2016 | Aghassian et al. |
| 9,232,903 B2 | 1/2016 | Pless et al. |
| 9,238,138 B2 | 1/2016 | Lee et al. |
| 9,240,630 B2 | 1/2016 | Joshi |
| 9,242,106 B2 | 1/2016 | Klosterman et al. |
| 9,248,279 B2 | 2/2016 | Chen et al. |
| 9,248,292 B2 | 2/2016 | Trier et al. |
| 9,248,302 B2 | 2/2016 | Mashiach et al. |
| 9,254,393 B2 | 2/2016 | Perryman et al. |
| 9,259,571 B2 | 2/2016 | Straka et al. |
| 9,259,582 B2 | 2/2016 | Joshi et al. |
| 9,259,584 B2 | 2/2016 | Bauhahn et al. |
| 9,265,941 B2 | 2/2016 | Van Den Biggelaar et al. |
| 9,265,958 B2 | 2/2016 | Joshi et al. |
| 9,289,616 B2 | 3/2016 | Koester |
| 9,295,841 B2 | 3/2016 | Fang et al. |
| 9,295,850 B2 | 3/2016 | Kallmyer |
| 9,314,613 B2 | 4/2016 | Mashiach |
| 9,314,628 B2 | 4/2016 | North et al. |

(56) References Cited

U.S. PATENT DOCUMENTS

| | | |
|---|---|---|
| 9,314,642 B2 | 4/2016 | Ozawa et al. |
| 9,320,847 B2 | 4/2016 | Rooney et al. |
| 9,320,899 B2 | 4/2016 | Parramon et al. |
| 9,320,908 B2 | 4/2016 | Fletcher et al. |
| 9,333,367 B2 | 5/2016 | Chen |
| 9,339,660 B2 | 5/2016 | Feldman et al. |
| 9,343,923 B2 | 5/2016 | Joshi |
| 9,352,161 B2 | 5/2016 | Thacker et al. |
| 9,370,664 B2 | 6/2016 | Marnfeldt et al. |
| 9,375,582 B2 | 6/2016 | Kaula et al. |
| 9,381,360 B2 | 7/2016 | Hershey |
| 9,387,331 B2 | 7/2016 | Zhao et al. |
| 9,387,332 B2 | 7/2016 | Zhao et al. |
| 9,393,423 B2 | 7/2016 | Parramon et al. |
| 9,393,428 B2 | 7/2016 | Nyberg, II et al. |
| 9,393,435 B2 | 7/2016 | Mashiach |
| 9,398,901 B2 | 7/2016 | Tischendorf et al. |
| 9,399,130 B2 | 7/2016 | Bonde et al. |
| 9,399,131 B2 | 7/2016 | Digiore et al. |
| 9,399,143 B2 | 7/2016 | Yamamoto et al. |
| 9,403,013 B2 | 8/2016 | Walker et al. |
| 9,403,020 B2 | 8/2016 | Wingeier |
| 9,403,021 B2 | 8/2016 | Dronov |
| 9,407,110 B2 | 8/2016 | Lui et al. |
| 9,409,029 B2 | 8/2016 | Perryman et al. |
| 9,435,830 B2 | 9/2016 | Joshi |
| 9,446,251 B1 | 9/2016 | Perryman et al. |
| 9,446,254 B2 | 9/2016 | Ozawa et al. |
| 9,449,501 B2 | 9/2016 | Grevious et al. |
| 9,452,288 B2 | 9/2016 | Whitehurst et al. |
| 9,457,186 B2 | 10/2016 | Gross |
| 9,463,321 B2 | 10/2016 | Bradley et al. |
| 9,463,323 B2 | 10/2016 | Lee et al. |
| 9,463,326 B2 | 10/2016 | Ranu |
| 9,468,771 B2 | 10/2016 | Griffith et al. |
| 9,468,772 B2 | 10/2016 | Demmer |
| 9,469,437 B2 | 10/2016 | Kamath |
| 9,474,905 B2 | 10/2016 | Doan et al. |
| 9,480,841 B2 | 11/2016 | Hershey et al. |
| 9,504,832 B2 | 11/2016 | Libbus et al. |
| 9,504,838 B2 | 11/2016 | Rao et al. |
| 9,517,344 B1 | 12/2016 | Bradley |
| 9,517,352 B2 | 12/2016 | Kast et al. |
| 9,522,270 B2 | 12/2016 | Perryman et al. |
| 9,533,148 B2 | 1/2017 | Carcieri |
| 9,533,153 B2 | 1/2017 | Libbus et al. |
| 9,533,154 B2 | 1/2017 | Kothandaraman et al. |
| 9,533,162 B2 | 1/2017 | Ter-petrosyan et al. |
| 9,555,257 B2 | 1/2017 | Mashiach et al. |
| 9,561,365 B2 | 2/2017 | Shi et al. |
| 9,585,642 B2 | 3/2017 | Dinsmoor et al. |
| 9,586,054 B2 | 3/2017 | Aghassian |
| 9,592,385 B2 | 3/2017 | Kaula et al. |
| 9,597,516 B2 | 3/2017 | Lee et al. |
| 9,597,517 B2 | 3/2017 | Moffitt |
| 9,597,521 B2 | 3/2017 | Plotkin et al. |
| 9,610,450 B2 | 4/2017 | Zhao |
| 9,616,230 B2 | 4/2017 | Grandhe |
| 9,623,244 B2 | 4/2017 | Kothandaraman |
| 9,623,245 B2 | 4/2017 | King et al. |
| 9,623,253 B2 | 4/2017 | Perryman et al. |
| 9,623,257 B2 | 4/2017 | Olson et al. |
| 9,630,231 B2 | 4/2017 | Kelsch et al. |
| 9,636,508 B2 | 5/2017 | Chen et al. |
| 9,643,022 B2 | 5/2017 | Mashiach et al. |
| 9,649,049 B2 | 5/2017 | Pless et al. |
| 9,649,493 B2 | 5/2017 | Mashiach |
| 9,653,941 B2 | 5/2017 | Dinsmoor et al. |
| 9,656,074 B2 | 5/2017 | Simon et al. |
| 9,656,076 B2 | 5/2017 | Trier et al. |
| 9,656,081 B2 | 5/2017 | Feldman et al. |
| 9,675,809 B2 | 6/2017 | Chow |
| 9,687,649 B2 | 6/2017 | Thacker |
| 9,700,725 B2 | 7/2017 | Zhu |
| 9,700,730 B2 | 7/2017 | Carbunaru et al. |
| 9,707,404 B2 | 7/2017 | Rao et al. |
| 9,713,707 B2 | 7/2017 | Oron et al. |
| 9,713,717 B2 | 7/2017 | Aghassian |
| 9,713,718 B2 | 7/2017 | Lamont et al. |
| 9,713,721 B2 | 7/2017 | Kothandaraman |
| 9,724,513 B2 | 8/2017 | Lane et al. |
| 9,731,116 B2 | 8/2017 | Chen |
| 9,737,703 B2 | 8/2017 | Carbunaru et al. |
| 9,737,714 B2 | 8/2017 | Zottola |
| 9,744,347 B2 | 8/2017 | Chen et al. |
| 9,744,362 B2 | 8/2017 | Steinke et al. |
| 9,744,365 B2 | 8/2017 | Davis et al. |
| 9,744,368 B2 | 8/2017 | Dinsmoor |
| 9,750,930 B2 | 9/2017 | Chen |
| 9,782,588 B2 | 10/2017 | Shi et al. |
| 9,782,593 B2 | 10/2017 | Parramon et al. |
| 9,782,596 B2 | 10/2017 | Vamos et al. |
| 9,789,314 B2 | 10/2017 | Perryman et al. |
| 9,789,321 B2 | 10/2017 | Dixit et al. |
| 9,789,324 B2 | 10/2017 | Bauhahn et al. |
| 9,802,038 B2 | 10/2017 | Lee et al. |
| 9,802,048 B2 | 10/2017 | Armstrong |
| 9,802,052 B2 | 10/2017 | Marnfeldt |
| 9,814,458 B2 | 11/2017 | North |
| 9,814,880 B2 | 11/2017 | Hershey et al. |
| 9,814,884 B2 | 11/2017 | Parker et al. |
| 9,839,786 B2 | 12/2017 | Rondoni et al. |
| 9,844,677 B2 | 12/2017 | Aghassian |
| 9,849,298 B2 | 12/2017 | Ozawa et al. |
| 9,855,436 B2 | 1/2018 | Dearden et al. |
| 9,861,812 B2 | 1/2018 | Gross et al. |
| 9,861,825 B2 | 1/2018 | Ozawa et al. |
| 9,867,989 B2 | 1/2018 | Blum et al. |
| 9,867,994 B2 | 1/2018 | Parramon |
| 9,878,158 B2 | 1/2018 | Hershey et al. |
| 9,913,980 B2 | 3/2018 | Ostroff et al. |
| 9,913,986 B2 | 3/2018 | Chow et al. |
| 9,913,990 B2 | 3/2018 | Ter-petrosyan et al. |
| 9,925,381 B2 | 3/2018 | Nassif |
| 9,929,584 B2 | 3/2018 | Aghassian et al. |
| 9,931,107 B2 | 4/2018 | Tischendorf et al. |
| 9,935,498 B2 | 4/2018 | Joshi |
| 9,943,685 B2 | 4/2018 | Ramesh et al. |
| 9,950,166 B2 | 4/2018 | Mashiach et al. |
| 9,950,173 B2 | 4/2018 | Doan |
| 9,950,179 B2 | 4/2018 | Bonde et al. |
| 9,956,419 B2 | 5/2018 | Bokil |
| 9,956,421 B2 | 5/2018 | Bunyan et al. |
| 9,974,965 B2 | 5/2018 | Perryman et al. |
| 9,981,130 B2 | 5/2018 | Lee |
| 9,993,645 B2 | 6/2018 | Walker et al. |
| 10,004,896 B2 | 6/2018 | Oron et al. |
| 10,010,717 B2 | 7/2018 | Aghassian et al. |
| 10,014,571 B2 | 7/2018 | Andersen et al. |
| 10,056,688 B2 | 8/2018 | Andersen et al. |
| 10,058,705 B2 | 8/2018 | Andersen et al. |
| 10,064,288 B2 | 8/2018 | Li et al. |
| 10,080,902 B2 | 9/2018 | Dinsmoor et al. |
| 10,105,540 B2 | 10/2018 | Oron et al. |
| 10,105,542 B2 | 10/2018 | Jiang et al. |
| 10,105,543 B2 | 10/2018 | Marnfeldt et al. |
| 10,118,040 B2 | 11/2018 | Zhu |
| 10,124,178 B2 | 11/2018 | Oron et al. |
| 10,143,845 B2 | 12/2018 | Kothandaraman |
| 10,149,976 B1 | 12/2018 | Andresen et al. |
| 10,173,062 B2 | 1/2019 | Parker |
| 10,177,609 B2 | 1/2019 | Olson et al. |
| 10,179,241 B2 | 1/2019 | Walker et al. |
| 10,182,807 B2 | 1/2019 | Bridgeman et al. |
| 10,195,425 B2 | 2/2019 | Ostroff et al. |
| 10,213,608 B2 | 2/2019 | Moffitt |
| 10,219,229 B1 | 2/2019 | Mulligan, IV |
| 10,226,637 B2 | 3/2019 | Aghassian et al. |
| 10,238,863 B2 | 3/2019 | Gross et al. |
| 10,449,374 B2 | 10/2019 | Oron et al. |
| 10,532,208 B2 | 1/2020 | Ostroff et al. |
| 10,583,284 B2 | 3/2020 | Peters et al. |
| 10,653,888 B2 | 5/2020 | Oron et al. |
| 2002/0077554 A1 | 6/2002 | Schwartz et al. |

(56) References Cited

U.S. PATENT DOCUMENTS

| | | |
|---|---|---|
| 2002/0099419 A1 | 7/2002 | Cohen et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0014016 A1 | 1/2003 | Purdy |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0114905 A1 | 6/2003 | Kuzma |
| 2003/0176898 A1 | 9/2003 | Gross et al. |
| 2003/0236557 A1 | 12/2003 | Whitehurst et al. |
| 2003/0236558 A1 | 12/2003 | Whitehurst et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0254624 A1 | 6/2004 | Johnson |
| 2004/0153074 A1 | 8/2004 | Bojarski et al. |
| 2004/0167584 A1 | 8/2004 | Carroll et al. |
| 2004/0249431 A1 | 12/2004 | Ransbury et al. |
| 2004/0254612 A1 | 12/2004 | Ezra et al. |
| 2005/0113894 A1 | 5/2005 | Zilberman et al. |
| 2005/0119714 A1* | 6/2005 | Sieracki ............ A61N 1/37247 607/48 |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2005/0182457 A1 | 8/2005 | Thrope et al. |
| 2005/0251061 A1 | 11/2005 | Schuler et al. |
| 2006/0085039 A1 | 4/2006 | Hastings et al. |
| 2006/0085042 A1 | 4/2006 | Hastings et al. |
| 2006/0095077 A1 | 5/2006 | Tronnes |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073353 A1* | 3/2007 | Rooney ............ A61N 1/0531 607/36 |
| 2007/0073354 A1 | 3/2007 | Knudson et al. |
| 2007/0083240 A1 | 4/2007 | Peterson et al. |
| 2007/0088397 A1* | 4/2007 | Jacobson ............ A61N 1/3704 607/9 |
| 2007/0173893 A1 | 7/2007 | Pitts |
| 2007/0208392 A1 | 9/2007 | Kuschner et al. |
| 2007/0219595 A1 | 9/2007 | He |
| 2007/0255369 A1 | 11/2007 | Bonde et al. |
| 2007/0293908 A1 | 12/2007 | Cowan et al. |
| 2007/0293912 A1 | 12/2007 | Cowan et al. |
| 2008/0004535 A1 | 1/2008 | Smits |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0065182 A1 | 3/2008 | Strother et al. |
| 2008/0071178 A1 | 3/2008 | Greenland et al. |
| 2008/0091255 A1 | 4/2008 | Caparso et al. |
| 2008/0103376 A1 | 5/2008 | Felder |
| 2008/0103407 A1 | 5/2008 | Bolea et al. |
| 2008/0103572 A1 | 5/2008 | Gerber |
| 2008/0109054 A1 | 5/2008 | Hastings et al. |
| 2008/0119911 A1 | 5/2008 | Rosero |
| 2008/0132964 A1 | 6/2008 | Cohen et al. |
| 2008/0183235 A1 | 7/2008 | Stancer et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0043356 A1 | 2/2009 | Longhini et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0182402 A1 | 7/2009 | Glukhovsky |
| 2009/0187221 A1 | 7/2009 | DiGiore et al. |
| 2009/0204170 A1 | 8/2009 | Hastings et al. |
| 2009/0204173 A1 | 8/2009 | Fang et al. |
| 2009/0234407 A1 | 9/2009 | Hastings et al. |
| 2009/0259280 A1 | 10/2009 | Wilkin et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1 | 1/2010 | Willis et al. |
| 2010/0049289 A1 | 2/2010 | Lund et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0280568 A1 | 11/2010 | Bulkes et al. |
| 2010/0305392 A1 | 12/2010 | Gross et al. |
| 2010/0324630 A1 | 12/2010 | Lee et al. |
| 2010/0331933 A1* | 12/2010 | Carbunaru ............ A61N 1/0556 607/116 |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0112605 A1 | 5/2011 | Fahey |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0224769 A1 | 9/2011 | Spenser et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0282412 A1 | 11/2011 | Glukhovsky et al. |
| 2011/0301670 A1 | 12/2011 | Gross |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0215285 A1 | 8/2012 | Tahmasian et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2013/0192611 A1 | 8/2013 | Taepke, II et al. |
| 2013/0325081 A1 | 12/2013 | Karst et al. |
| 2013/0325084 A1 | 12/2013 | Lee |
| 2014/0214134 A1 | 7/2014 | Peterson |
| 2014/0296940 A1 | 10/2014 | Gross |
| 2015/0004709 A1 | 1/2015 | Nazarpoor |
| 2015/0018598 A1 | 1/2015 | Nabutovsky et al. |
| 2015/0018728 A1 | 1/2015 | Gross et al. |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0148878 A1 | 5/2015 | Yoo et al. |
| 2015/0174406 A1 | 6/2015 | Lamensdorf et al. |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0361544 A1 | 12/2016 | Oron et al. |
| 2017/0007829 A1 | 1/2017 | Gross |
| 2017/0119435 A1 | 5/2017 | Gross et al. |
| 2017/0128724 A1 | 5/2017 | Oron et al. |

(56) References Cited

U.S. PATENT DOCUMENTS

| | | | |
|---|---|---|---|
| 2017/0136232 | A1 | 5/2017 | Oron et al. |
| 2017/0224996 | A1 | 8/2017 | Oron et al. |
| 2017/0232255 | A1 | 8/2017 | Kent et al. |
| 2017/0296426 | A1 | 10/2017 | Oron et al. |
| 2018/0126157 | A1 | 5/2018 | Gross et al. |
| 2018/0140849 | A1 | 5/2018 | Oron et al. |
| 2019/0070420 | A1 | 3/2019 | Oron et al. |
| 2019/0217085 | A1 | 7/2019 | Oron et al. |
| 2020/0046974 | A1 | 2/2020 | Ostroff et al. |

FOREIGN PATENT DOCUMENTS

| | | |
|---|---|---|
| CN | 101947357 | 1/2011 |
| CN | 203154605 | 8/2013 |
| DE | 102008054403 | 6/2010 |
| EP | 0 688 577 | 12/1995 |
| EP | 1533000 | 5/2005 |
| EP | 1703638 | 11/2012 |
| WO | 1998/010832 | 3/1998 |
| WO | 1999/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 | 7/2013 |
| WO | 2013/111137 | 8/2013 |
| WO | 2013/156038 | 10/2013 |
| WO | 2013/164829 | 11/2013 |
| WO | 2014/068577 A2 | 5/2014 |
| WO | 2014/068577 A3 | 5/2014 |
| WO | 2014/081978 | 5/2014 |
| WO | 2014/087337 | 6/2014 |
| WO | 2014/167568 | 10/2014 |
| WO | 2015/004673 | 1/2015 |
| WO | 2016/028608 | 2/2016 |
| WO | 2016/157183 | 10/2016 |
| WO | 2016/172109 | 10/2016 |

OTHER PUBLICATIONS

U.S. Appl. No. 61/662,073, filed Jun. 20, 2012.
U.S. Appl. No. 61/591,024, filed Jan. 26, 2012.
U.S. Appl. No. 14/374,375, filed Jul. 24, 2014, published as 2015/0018728.
Office Action dated Feb. 1, 2022, issued by the U.S. Patent and Trademark Office in U.S. Appl. No. 17/486,072.
An Office Action dated Jun. 17, 2021, which issued during the prosecution of U.S. Appl. No. 16/363,256.
An Office Action summarized English translation and Search Report dated May 6, 2021, which issued during the prosecution of Chinese Patent Application No. 201610957461.7.
An Office Action dated May 6, 2021, which issued during the prosecution of Chinese Patent Application No. 201610957551.6.
An Office Action dated Jun. 1, 2021, which issued during the prosecution of Chinese Patent Application No. 201610909174.9.
An Office Action dated Aug. 13, 2021, which issued during the prosecution of Chinese Patent Application No. 201610957461.7.
An Office Action dated Dec. 21, 2020, which issued during the prosecution of U.S. Appl. No. 16/363,256.
An Office Action dated Dec. 2, 2020, which issued during the prosecution of U.S. Appl. No. 16/166,383.
C. de Balthasar, G. Cosendai, M. Hansen, D. Canfield, L. Chu, R. Davis, and J. Schulman, "Attachment of leads to RF-BION® microstimulators."Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 17, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.

(56) References Cited

OTHER PUBLICATIONS

Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. And Psych. 1980, 43, 713-718.
Jobges et al., Vibratory proprioceptive stimulation affects Parkinsonian tremor. Parkinsonism & Related Disorders, 8(3), 171-176, Jan 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/050069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).

Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, Ed M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
An Office Action dated May 19, 2017, which issued during the prosecution of U.S. Appl. No. 14/935,941.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
A Notice of Allowance dated Jun. 9, 2014, which issued during the prosecution of U.S. Appl. No. 12/796,102.
Notice of Allowance dated Sep. 1, 2017, which issued during the prosecution of U.S. Appl. No. 14/649,873.
Brindley (1983) A technique for anodally blocking large nerve fibers.
An Office Action dated Sep. 22, 2016, which issued during the prosecution of U.S. Appl. No. 14/374,375.
DJOGlobal.com—Interferential Current Therapy (IFC).
A Notice of Allowance dated Apr. 25, 2014, which issued during the prosecution of U.S. Appl. No. 13/528,433.
An Office Action dated Sep. 26, 2013, which issued during the prosecution of U.S. Appl. No. 13/528,433.
U.S. Appl. No. 60/985,353, filed Nov. 5, 2007.
An Office Action dated Apr. 4, 2017, which issued during the prosecution of U.S. Appl. No. 14/601,604.
electrotherapy.org—Interferential Therapy.
An Office Action dated Feb. 27, 2017, which issued during the prosecution of U.S. Appl. No. 14/649,873.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.

(56) References Cited

OTHER PUBLICATIONS

An Office Action dated Oct. 30, 2015, which issued during the prosecution of U.S. Appl. No. 14/226,723.
Notice of Allowance dated Jun. 15, 2017, which issued during the prosecution of U.S. Appl. No. 14/939,418.
Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472.
UCLA Team Reports Initial Success with Trigeminal Nerve Stimulation epilepsy. https://web.archive.org/web/20121020145122/https://www.epilepsy.com/epilepsy/newsletter/apr09_STIM.
Kucklick, Theodore R., ed. *The medical device R&D handbook.* Chapter 3—Intro to needles and cannulae. CRC Press, 2012.
Szmurlo, R., Starzynski, J., Wincenciak, S. and Rysz, A. (2009) 'Numerical model of vagus nerve electrical stimulation', *COMPEL— The international journal for computation and mathematics in electrical and electronic engineering*, 28(1), pp. 211-220.
An Office Action dated Apr. 5, 2017, which issued during the prosecution of U.S. Appl. No. 14/374,375.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Reggiani et al. "Biophysical effects of high frequency electrical field on muscle fibers in culture." (2009) pp. 49-56.
https://www.uroplasty.com/files/pdf/20158.pdf Brochure (Downloaded Oct. 16, 2014).
An Office Action dated Aug. 8, 2016, which issued during the prosecution of U.S. Appl. No. 14/735,741.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
An Office Action dated Dec. 12, 2016, which issued during the prosecution of U.S. Appl. No. 14/939,418.
Notice of Allowance dated Mar. 22, 2017, which issued during the prosecution U.S. Appl. No. 14/939,418.
Injecta 2013 GmbH catalogue.
An Office Action dated Feb. 13, 2017, which issued during the prosecution of U.S. Appl. No. 14/601,604.
U.S. Appl. No. 61/733,995, filed Dec. 6, 2012.
Alo, Kenneth M., et al. "Lumbar and sacral nerve root stimulation (NRS) in the treatment of chronic pain: a novel anatomic approach and neuro stimulation technique." Neuromudulation: Technology at the Neural Interface 2.1 (1999): 23-31.
European Search Report dated Mar. 10, 2017, which issued during the prosecution of Applicant's European App No. 16196864.9.

An Office Action dated Nov. 21, 2016, which issued during the prosecution of U.S. Appl. No. 14/601,626.
Stuart, R. Morgan, and Christopher J. Winfree. "Neurostimulation techniques for painful peripheral nerve disorders." Neurosurgery Clinics of North America 20.1 (2009): 111-120.
European Search Report dated Feb. 3, 2017, which issued during the prosecution of Applicant's European App No. 16196878.9.
Gofeld, Michael, and John G. Hanlon. "Ultrasound-Guided Placement of a Paddle Lead Onto Peripheral Nerves: Surgical Anatomy and Methodology." Neuromodulation: Technology at the Neural Interface 17.1 (2014): 48-53.
An Office Action dated Dec. 6, 2017, which issued during the prosecution of U.S. Appl. No. 14/601,604.
An Office Action dated Dec. 26, 2017, which issued during the prosecution of U.S. Appl. No. 14/935,941.
An Office Action dated Jan. 8, 2018, which issued during the prosecution of U.S. Appl. No. 14/935,941.
An Office Action dated Mar. 5, 2018, which issued during the prosecution of U.S. Appl. No. 15/360,501.
An Office Action dated Nov. 30, 2017, which issued during the prosecution of U.S. Appl. No. 15/726,971.
A Notice of Allowance dated Feb. 15, 2018, which issued during the prosecution of U.S. Appl. No. 14/601,604.
A Notice of Allowance dated Jul. 16, 2018, which issued during the prosecution of U.S. Appl. No. 15/360,501.
An Office Action dated Jun. 4, 2018, which issued during the prosecution of U.S. Appl. No. 15/860,385.
Notice of Allowance dated Oct. 22, 2018, which issued during the prosecution of U.S. Appl. No. 15/860,385.
An Office Action dated Jun. 26, 2019, which issued during the prosecution of U.S. Appl. No. 15/395,257.
An Office Action dated Dec. 5, 2018, which issued during the prosecution of U.S. Appl. No. 15/581,390.
An Office Action dated Feb. 7, 2019, which issued during the prosecution of U.S. Appl. No. 15/706,956.
An Office Action dated Jul. 24, 2020, which issued during the prosecution of U.S. Appl. No. 16/363,256.
An Office Action dated Apr. 22, 2019, which issued during the prosecution of U.S. Appl. No. 15/638,924.
An Office Action dated Oct. 11, 2018, which issued during the prosecution of U.S. Appl. No. 15/638,924.
Notice of Allowance dated Jan. 17, 2020, which issued during the prosecution of U.S. Appl. No. 15/638,924.
An Interview Summary dated Mar. 5, 2019, which issued during the prosecution of U.S. Appl. No. 15/638,924.
An Advisory Action and an Interview Summary dated Sep. 16, 2019, which issued during the prosecution of U.S. Appl. No. 15/638,924.
Notice of Allowance dated Jun. 17, 2019, which issued during the prosecution of U.S. Appl. No. 15/581,390.
Notice of Allowance dated May 20, 2020, which issued during the prosecution of U.S. Appl. No. 16/183,783.
An Advisory Action issued in U.S. Appl. No. 17/486,072, dated Sep. 27, 2022.
Office Action dated Dec. 6, 2022 issued by the U.S. Patent and Trademark Office in U.S. Appl. No. 17/486,072.

* cited by examiner

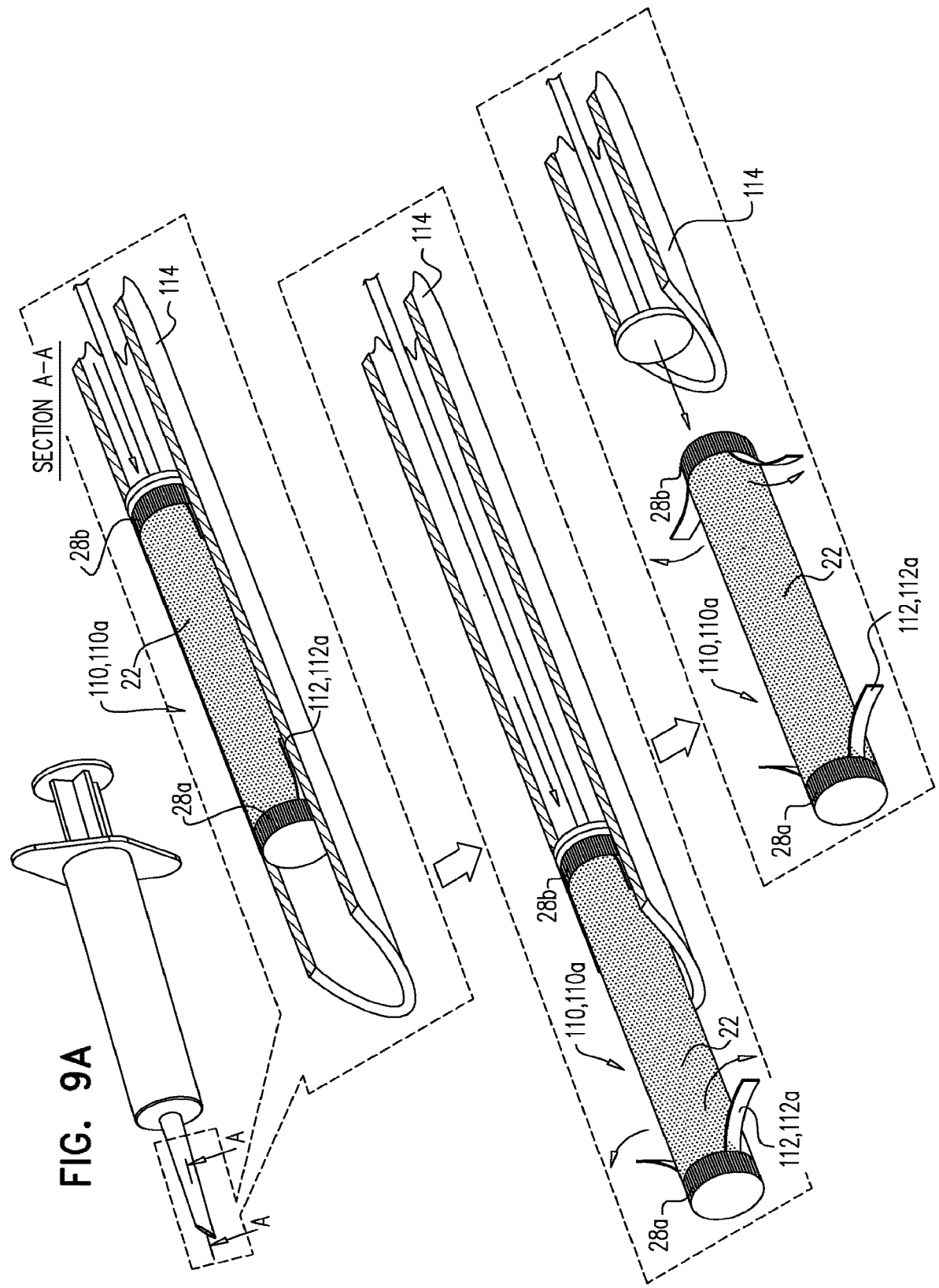

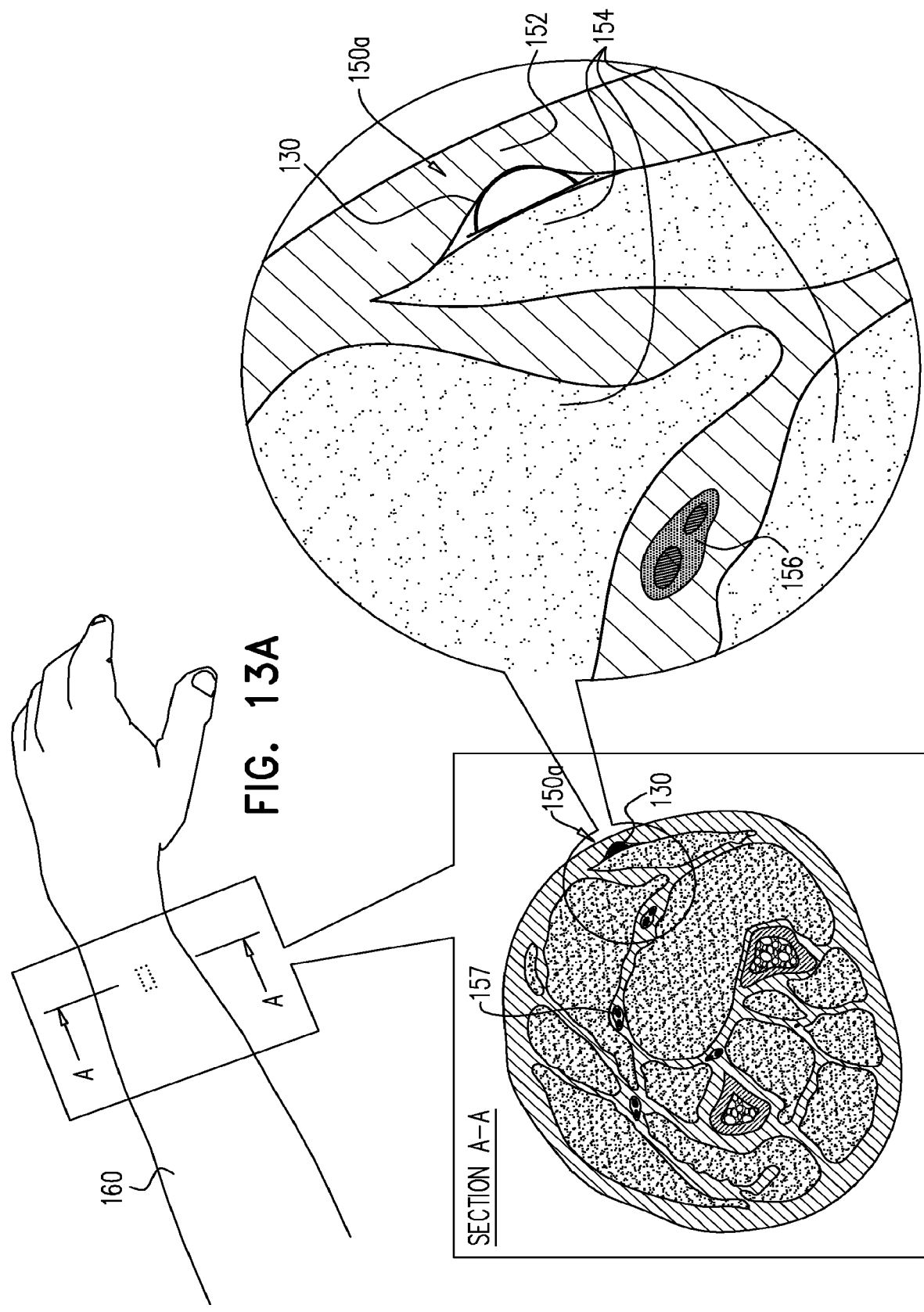

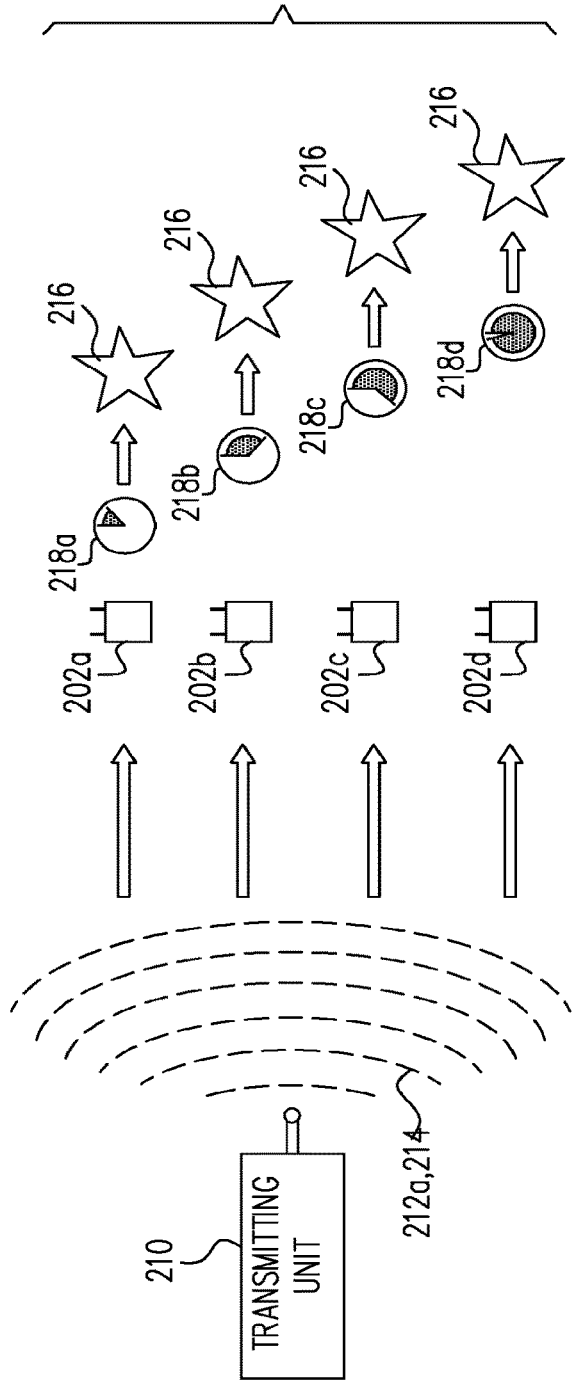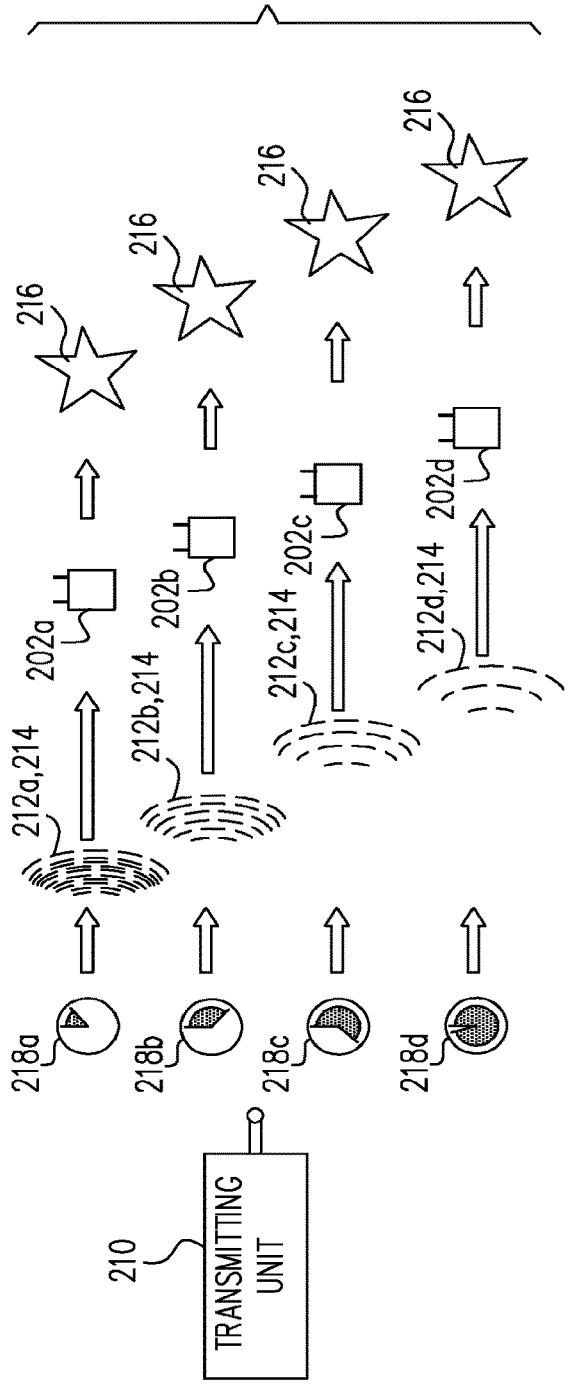

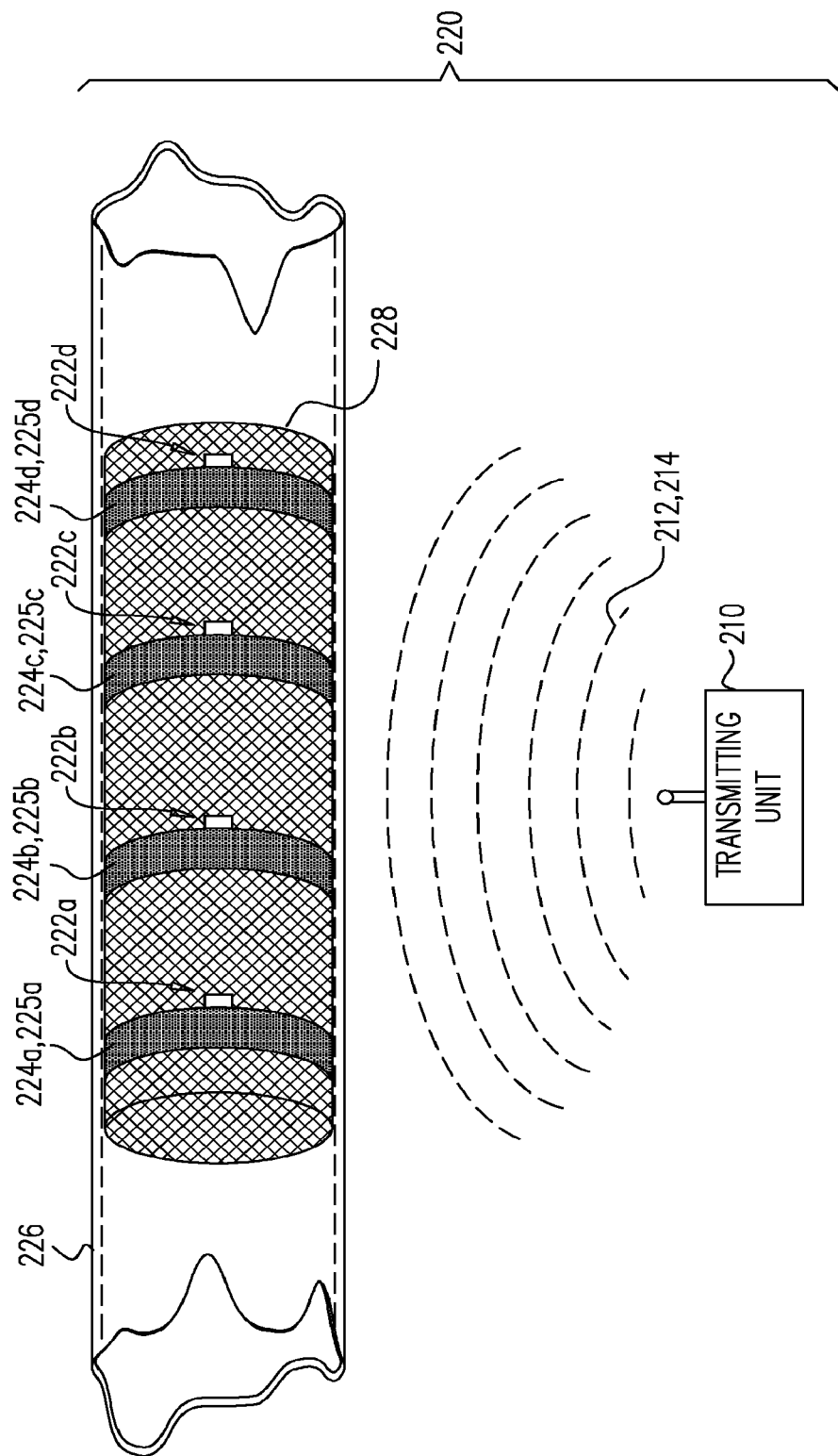

US 11,648,410 B2

WIRELESS NEUROSTIMULATORS

CROSS-REFERENCE[[S]] TO RELATED APPLICATIONS

The present application is a Continuation of U.S. patent application Ser. No. 15/638,924 to Oron et al., filed Jun. 30, 2017, entitled "Wireless Neurostimulators," now U.S. Pat. No. 10,653,888, which is a Continuation of U.S. patent application Ser. No. 14/374,375 to Gross et al., filed Jul. 24, 2014, entitled "Wireless Neurostimulators", which published as US 2015/0018728, and which is the US National Phase of International Application PCT/IL2013/050069 to Gross et al., filed Jan. 24, 2013, which published as WO 2013/111137, and which (1) claims priority from (a) U.S. Provisional Application 61/591,024 to Gross, filed Jan. 26, 2012, and (b) U.S. Provisional Application 61/662,073 to Gross et al., filed Jun. 20, 2012, and (2) is related to (a) U.S. application Ser. No. 12/796,102 to Gross, filed Jun. 8, 2010, now U.S. Pat. No. 8,788,045 and (b) U.S. application Ser. No. 13/528,433 to Gross, filed Jun. 20, 2012, now U.S. Pat. No. 8,755,893, all of which are assigned to the assignee of the present application, and all of which are incorporated herein by reference.

FIELD OF THE INVENTION

The present invention relates generally to medical devices, and specifically to apparatus and methods for neurostimulation.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Other disorders may cause pain to adjacent tissues.

Neurostimulation is a clinical tool used to treat various neurological disorders. This technique involves modulation of the nervous system by electrically activating fibers in the body.

SUMMARY OF APPLICATIONS

For some applications of the present invention, a system for wireless neurostimulation comprises a circuitry unit, coupled to at least two electrodes. According to one application of the present invention, one electrode is disposed on an outer surface of the circuitry unit, whereas a second electrode is coupled to a nerve cuff. According to another application of the present invention, the at least two electrodes are coupled to the nerve cuff (or to two or more nerve cuffs). Typically, the circuitry unit and nerve cuff are coupled by a lead.

Typically, the circuitry unit comprises circuitry for receiving and processing energy for driving the electrodes, and this energy is received from a site outside of the circuitry unit. For example, the site may be inside, or outside, of the subject's body.

For some applications of the present invention, the circuitry unit is coupled via leads to two nerve cuffs. Typically, each nerve cuff comprises one or more electrodes.

For some applications of the present invention, the circuitry unit is coupled via a lead to an antenna.

For some applications of the present invention, the circuitry unit is coupled via a lead to an array of microelectrodes. For some applications of the present invention, the microelectrodes are disposed on the circuitry unit itself.

There is therefore provided, in accordance with an application of the present invention, apparatus for applying a treatment to at least one tissue of a subject, the apparatus including:

a transmitting unit, configured to transmit a wireless power signal; and a first implant and a second implant, each of the implants being configured to receive the power signal and to apply the treatment asynchronously to each other, in response to the power signal.

In an application, the first implant includes a plurality of first implants, the first implants being configured to apply the treatment synchronously with respect to each other, in response to the power signal.

In an application, at least one of the implants includes a subcutaneously-implantable implant.

In an application, the implants are configured to receive power from the power signal.

In an application, the first implant does not include a power supply that is able to continuously power the first implant for a period greater than one minute.

In an application, the second implant does not include a power supply that is able to continuously power the second implant for a period greater than one minute.

In an application:

the first implant is configured to receive the power signal, and to apply the treatment after a first duration following receiving the power signal, and the second implant is configured to receive the power signal, and to apply the treatment after a second duration following receiving the power signal, the second duration being longer than the first duration.

In an application:

the transmitting unit is configured to transmit a plurality of wireless power signals, including at least first and second wireless power signals, the first implant is configured to receive power from the first power signal, and the second implant is configured to receive power from the second power signal.

In an application, the transmitting unit is configured to transmit the first and second power signals asynchronously.

In an application, the first implant is configured to apply the treatment in response to the first power signal, and the second implant is configured to apply the treatment in response to the second power signal.

In an application:

the transmitting unit is configured to configure the first and second power signals to have respective first and second characteristics that differ from one another, the first implant is configured to receive power from the first power signal, in response to an effect of the first characteristic on the first implant, and the second implant is configured to receive power from the second power signal, in response to an effect of the second characteristic on the second implant.

In an application:

the first and second characteristics include respective first and second frequencies, and the transmitting unit is configured to configure the first and second power signals to have the respective first and second frequencies.

In an application:

the first and second characteristics include respective first and second codes, and the transmitting unit is configured to configure the first and second power signals to have the respective first and second codes.

In an application, the transmitting unit is configured to transmit a control signal, and each implant is configured to apply the treatment in response to the control signal.

In an application, the transmitting unit is configured to modulate the control signal onto the power signal.

In an application:

the first implant is configured to receive the control signal, and to apply the treatment after a first duration following receiving the control signal, and the second implant is configured to receive the control signal, and to apply the treatment after a second duration following receiving the control signal, the second duration being longer than the first duration.

In an application, the transmitting unit is configured to configure the power signal to be at least as long as the second duration.

In an application:

the transmitting unit is configured to transmit a plurality of control signals, including at least first and second control signals, the first implant is configured to apply the treatment in response to the first control signal, and the second implant is configured to apply the treatment in response to the second control signal.

In an application, the transmitting unit is configured to transmit the power signal at least during the transmission of both the first and the second control signals.

In an application, the first and second implants are each configured to apply the treatment while receiving the first and second control signals, respectively.

In an application, the apparatus includes a plurality of implants that include at least the first and second implants, and the apparatus is configured such that each implant is implantable at a pre-selected distance from another one of the implants.

In an application, the apparatus further includes a support to which at least two of the implants are couplable, at the pre-selected distance from one another.

In an application, the support includes a stent, configured to be implanted in a tubular structure of the subject.

In an application, the support includes a cuff, configured to be disposed around a tubular structure of the subject.

In an application, the support includes a delivery device, configured to facilitate the implantation at the pre-selected distance.

In an application:

the delivery device has a distal portion and a proximal portion, the delivery device includes a release member at the proximal portion, and the at least two of the implants are decouplable from the distal portion of the delivery device, by activation of the release member at the proximal portion.

There is further provided, in accordance with an application of the present invention, apparatus for applying a treatment to a tissue of a subject, the apparatus including a medical implant, the implant including a plurality of components, at least one of the components including a circuitry unit, which is injectably implantable into the subject, at least one of the components including an effector element, which is not injectably implantable into the subject, and which is flexibly coupled to the circuitry unit.

In an application, the implant does not include a power supply that is able to continuously power the implant for a period greater than one minute.

In an application, the effector element includes an electrode.

In an application, the apparatus further includes a nerve cuff, the nerve cuff including the electrode.

There is further provided, in accordance with an application of the present invention, apparatus for treating a condition of a subject, the apparatus including an implant, the implant:

having a skin-facing side on which at least one effector element is disposed, having an opposing side on which no effector element is disposed, being configured to be implanted at an implantation site that is deeper than a surface of skin of the subject, such that the skin-facing side faces superficially, and including a circuitry unit, configured to drive the effector element to apply a treatment that stimulates sensory fibers of the skin of the subject.

In an application, the implant is configured to be implanted subcutaneously.

In an application, the implant is configured to be implanted intradermally.

In an application, the implant does not include a power supply that is able to continuously power the implant for a period greater than one minute.

In an application, the effector element includes a vibrating element, and the circuitry unit is configured to drive the vibrating element to stimulate the sensory fibers, by driving the vibrating element to vibrate.

In an application, the implant is configured not to induce contraction of a muscle of the subject.

In an application, the effector element is disposed farther than 1 mm from any lateral edge of the implant.

In an application, the effector element is disposed farther than 2 mm from any lateral edge of the implant.

In an application, the effector element is disposed farther than 5 mm from any lateral edge of the implant.

In an application, the apparatus further includes a transmitting unit, configured to transmit wireless power, and the implant is configured to receive the wireless power.

In an application, the implant is configured to apply the treatment in response to receiving the wireless power.

In an application, the implant is configured to apply the treatment only when the implant receives the wireless power.

In an application, the implant has a height, from the skin-facing side to the opposing side of the implant, that is smaller than both a longest length and a width of the implant.

In an application, the implant is generally flat.

In an application, the implant is generally shaped to define a prism that has a transverse cross-sectional shape that is generally semicircular.

In an application, the implant is generally shaped to define a prism that has a transverse cross-sectional shape that is generally elliptical.

In an application, the implant is configured not to directly initiate action potentials in a nerve of the subject.

In an application, the implant is configured not to directly initiate the action potentials in the nerve of the subject, by being configured to apply the treatment that stimulates sensory fibers of the skin of the subject from an implantation site that is farther than 1 cm from the nerve of the subject.

In an application, the implant is configured not to directly initiate the action potentials in the nerve of the subject, by being configured to apply the treatment that stimulates sensory fibers of the skin of the subject from an implantation site that is farther than 2 cm from the nerve of the subject.

In an application, the implant is configured not to directly initiate the action potentials in the nerve of the subject, by being configured to apply the treatment that stimulates sensory fibers of the skin of the subject from an implantation site that is farther than 3 cm from the nerve of the subject.

In an application, the effector element includes an electrode, and the circuitry unit is configured to drive the electrode to stimulate the sensory fibers, by driving a current through the electrode.

In an application, the implant is configured not to directly initiate the actions potentials in the nerve of the subject, by the circuitry unit being configured to configure the current not to directly initiate the action potentials in the nerve of the subject.

In an application, the implant is configured not to directly initiate action potentials in the nerve of the subject, by being configured to direct the treatment superficially from the implant.

In an application, the implant is configured to direct the treatment superficially, by the effector element being disposed on the skin-facing superficial side of the implant.

In an application, the implant is configured to direct the treatment superficially, by the implant including an insulating member, disposed on the opposing side of the implant.

In an application, the implant is configured to induce a sensation in the skin of the subject.

In an application, the effector element includes an electrode, and the circuitry unit is configured to drive the electrode to stimulate the sensory fibers, by driving a current through the electrode.

In an application, the implant is configured, when implanted at the implantation site, to drive the current superficially to the implant.

In an application, the implant further includes an accelerometer, configured to detect movement of at least the implant.

In an application, the implant is configured to be implanted in a limb of the subject, and the accelerometer is configured to detect movement of the limb of the subject.

In an application, the implant is configured to be implanted in a limb of the subject that is affected by tremor, and the accelerometer is configured to detect the tremor of the limb of the subject.

In an application, the circuitry unit is configured to configure the treatment at least in part responsively to the detection of the movement.

In an application, the movement has a phase, and the circuitry unit is configured to configure the treatment by applying the treatment in phase with the phase of the movement.

In an application, the circuitry unit is configured to configure the treatment by altering an angle of phase of the treatment with respect to the phase of the movement.

In an application, the treatment includes application of an electrical current, and the circuitry unit is configured to configure the treatment by configuring one or more parameters of the current selected from the group consisting of: an amplitude of the current, a frequency of the current, a pulse-width of the current, and an on-off pattern of the current.

There is further provided, in accordance with an application of the present invention, apparatus for applying a treatment to a tissue of a subject, the apparatus including a medical implant, the implant including:
an injectable circuitry unit;
at least one effector element, coupled to the circuitry unit, and configured to be driven by the circuitry unit to apply the treatment;
at least one anchor, coupled to the circuitry unit, and having a delivery configuration, and an anchoring configuration in which, when the implant is implanted in the tissue of the subject, the anchor inhibits movement of the implant along a longitudinal axis thereof.

In an application, the implant does not include a power supply that is able to continuously power the implant for a period greater than one minute.

In an application, the apparatus further includes a delivery device, shaped to define a lumen, and:
the implant is disposable in, slidable through, and slidable out of the lumen of the delivery device, and is deliverable to the tissue of the subject by sliding the device out of the lumen of the delivery device, and
the anchors are configured:
when the implant is disposed in the lumen of the delivery device, to be constrained by the delivery device in the delivery configuration, and
when the implant is slid out of the lumen of the delivery device, to automatically move toward the anchoring configuration.

There is further provided, in accordance with an application of the present invention, apparatus for applying at least one treatment to a subject, the apparatus including:
a first transmitting unit, configured to transmit a first wireless signal;
a second transmitting unit, configured to transmit a second wireless signal;
a first implant, configured to be implanted at a first implantation site of the subject, and to apply the at least one treatment to the subject in response to the first wireless signal; and
a second implant, configured to be implanted at a second implantation site of the subject, to apply the at least one treatment to the subject in response to the second wireless signal, and not to apply the at least one treatment to the subject in response to the first wireless signal.

In an application, each implant does not include a power supply that is able to continuously power the implant for a period greater than one minute.

In an application, the first transmitting unit is configured to configure the first wireless signal to have a first frequency, and the second transmitting unit is configured to configure the second wireless signal to have a second frequency that is different from the first frequency.

In an application:
the first and second wireless signals include first and second wireless power signals,
the first implant is configured to receive power from the first power signal, and
the second implant is configured to receive power from the second power signal, and not to receive power from the first power signal.

In an application, the transmitting units are configured to be coupled to the subject.

In an application, the implants are configured to be implanted such that the implants are disposed, at least part of the time, within 30 cm of each other.

In an application, the first implant is configured to be implanted in a first leg of the subject and the second implant is configured to be implanted in a second leg of the subject.

In an application, the first transmitting unit is configured to be coupled to the first leg of the subject, and the second transmitting unit is configured to be coupled to the second leg of the subject.

There is further provided, in accordance with an application of the present invention, a method for use with a medical implant for implanting at a tissue of a subject, the method including:

percutaneously delivering at least part of at least one temporary electrode to the tissue of the subject;

electrically stimulating the tissue of the subject for between 1 and 120 minutes, using the temporary electrode;

receiving information indicative of a desired change in a sensation experienced by the subject between a time before a start of the electrical stimulation and a time after a start of the electrical stimulation; and at least in part responsively to the received information, implanting the medical implant at the tissue of the subject.

In an application, electrically stimulating includes electrically stimulating the tissue for between 10 and 30 minutes.

In an application, receiving the information indicative of the desired change in the sensation includes receiving information indicative of a desired change in a pain experienced by the subject.

In an application, receiving the information indicative of the desired change in the sensation includes receiving information indicative of paresthesia induced by the electrical stimulation of the tissue of the subject.

In an application, the method further includes:

receiving a first value indicative of the factor before the electrical stimulation; and receiving a second value indicative of the factor after the electrical stimulation, and receiving the information indicative of the change in the factor includes receiving a value indicative of a difference between the first value and the second value.

In an application, receiving the information indicative of the change in the factor, includes receiving information indicative of a change in pain experienced by the subject.

In an application, the tissue of the subject includes a tibial nerve of the subject, and stimulating the tissue of the subject includes stimulating the tibial nerve of the subject.

There is further provided, in accordance with an application of the present invention, a method for applying a treatment to at least one tissue of a subject, the method including:

transmitting a wireless power signal;

receiving the power signal using a first implant and a second implant, each of the implants being implanted at the tissue of the subject; and in response to receiving the power signal, asynchronously applying the treatment using the first implant and using the second implant.

In an application, transmitting includes extracorporeally transmitting the wireless power signal.

In an application, receiving the power signal includes subcutaneously receiving the power signal using the first and second implants.

In an application, receiving the power signal includes receiving the power signal using the first and second implants, after they have been transluminally implanted.

In an application, asynchronously applying the treatment includes:

receiving the power signal using the first implant, and applying the treatment using the first implant after a first duration following receiving the power signal; and receiving the power signal using the second implant, and applying the treatment using the second implant after a second duration following receiving the power signal, the second duration being longer than the first duration.

In an application:

transmitting the power signal includes transmitting a plurality of wireless power signals, including at least first and second wireless power signals, and receiving the power signal includes receiving the first power signal using the first implant, and receiving the second power signal using the second implant.

In an application, transmitting includes transmitting the first and second power signals asynchronously.

In an application, applying the treatment includes:

applying the treatment using the first implant in response to the first power signal and not in response to the second power signal; and applying the treatment using the second implant in response to the second power signal and not in response to the first power signal.

In an application, applying the treatment includes:

applying the treatment using the first implant while receiving the first power signal;

and applying the treatment using the second implant while receiving the second power signal.

In an application:

transmitting the first and second power signals includes transmitting first and second power signals that have respective first and second characteristics that differ from one another, receiving power from the first power signal, using the first implant, in response to an effect of the first characteristic on the first implant, and receiving power from the second power signal, using the second implant, in response to an effect of the second characteristic on the second implant.

In an application:

the first and second characteristics include respective first and second frequencies, and transmitting includes transmitting first and second power signals that have the respective first and second frequencies.

In an application:

the first and second characteristics include respective first and second codes, and transmitting includes transmitting first and second power signals that have the respective first and second codes.

In an application, the method further includes:

transmitting a control signal; and receiving the control signal using the first and second implants, and asynchronously applying the treatment includes, in response to the control signal, asynchronously applying the treatment using the first implant and using the second implant.

In an application, transmitting the control signal includes modulating the control signal onto the power signal.

In an application, asynchronously applying the treatment includes:

receiving the control signal using the first implant, and applying the treatment using the first implant after a first duration following receiving the control signal; and receiving the control signal using the second implant, and applying the treatment using the second implant after a second duration following receiving the control signal, the second duration being longer than the first duration.

In an application, transmitting the power signal includes transmitting the power signal for a duration that is at least as long as the second duration.

In an application:
transmitting the control signal includes transmitting a plurality of control signals, including at least first and second control signals, and
asynchronously applying the treatment includes:
applying the treatment using the first implant in response to the first control signal; and
applying the treatment using the second implant in response to the second control signal.

In an application, transmitting the power signal includes transmitting the power signal at least during the transmission of both the first and the second control signals.

In an application, applying the treatment using the first implant includes applying the treatment using the first implant while receiving the first control signal, and applying the treatment using the second implant includes applying the treatment using the second implant while receiving the second control signal.

In an application, receiving the power signal includes receiving the power signal using the first and second implants, after each of the implants has been implanted at a pre-selected distance from the other one of the implants.

In an application, the implants are couplable to a support at the pre-selected distance from one another, and receiving the power signal includes receiving the power signal using the first and second implants, after the support has been implanted in a tubular structure of the subject.

In an application, the support includes a stent, and receiving the power signal includes receiving the power signal using the first and second implants, after the stent has been implanted in the tubular structure of the subject.

In an application, the support includes a cuff, and receiving the power signal includes receiving the power signal using the first and second implants, after the cuff has been implanted in the tubular structure of the subject.

In an application, the support includes a delivery device, and receiving the power signal includes receiving the power signal using the first and second implants, after the stent has been implanted using the delivery device.

In an application, receiving the power signal includes receiving the power signal using the first and second implants, after the stent has been decoupled from the delivery device.

There is further provided, in accordance with an application of the present invention, a method for treating a condition of a subject, the method including:
driving a subcutaneously-implanted effector element to apply a treatment that stimulates sensory fibers of skin of the subject; and
using an inhibiting element, inhibiting direct stimulation of a nerve of the subject that is closest to the effector element, during the application of the treatment by the effector element.

In an application, inhibiting the direct stimulation of the nerve includes preventing direct initiation of action potentials in the nerve.

In an application, inhibiting the direct stimulation of the nerve includes preventing direct initiation of action potentials in an ulnar nerve of the subject.

In an application, inhibiting the direct stimulation of the nerve includes preventing direct initiation of action potentials in a median nerve of the subject.

In an application, inhibiting the direct stimulation of the nerve includes preventing direct initiation of action potentials in a nerve of the subject that is disposed deeper than the inhibiting element.

In an application, driving the effector element to apply the treatment includes driving the effector element to vibrate.

In an application, inhibiting further includes inhibiting direct induction of contraction of a muscle of the subject.

In an application, driving the effector element includes driving the effector element using an implanted circuitry unit.

In an application, driving the effector element includes wirelessly driving the effector element.

In an application, inhibiting the direct stimulation of the nerve includes directing the treatment away from the nerve.

In an application, directing the treatment includes directing the treatment superficially.

In an application, driving the effector element includes driving the effector element after an implant that includes the effector element has been subcutaneously implanted in the subject.

In an application, the effector element is disposed only on a skin-facing side of the implant, and inhibiting the direct stimulation of the nerve includes driving the effector element that is disposed on the skin-facing side of the implant.

In an application, inhibiting the direct stimulation of the nerve includes insulating the nerve from the treatment using the inhibiting element.

In an application, insulating includes electrically insulating the nerve from the treatment.

In an application, insulating includes mechanically insulating the nerve from the treatment.

In an application, driving the effector element includes driving the effector element after an implant that (1) has a height from a lower portion to an upper portion of the implant that is smaller than both a longest length and a width of the implant, and (2) includes the effector element, has been subcutaneously implanted in the subject.

In an application, driving the effector element includes driving the effector element after an implant that (1) is generally shaped to define a prism that has a transverse cross-sectional shape that is generally semicircular, and (2) includes the effector element, has been subcutaneously implanted in the subject.

In an application, driving the effector element includes driving the effector element after an implant that (1) is generally shaped to define a prism that has a transverse cross-sectional shape that is generally elliptical, and (2) includes the effector element, has been subcutaneously implanted in the subject.

In an application, driving the effector element includes driving the effector element after an implant that (1) is generally flat, and (2), includes the effector element, has been subcutaneously implanted in the subject.

In an application, inhibiting the direct stimulation of the nerve includes inhibiting the direct stimulation of the nerve by driving the effector element after an implant that includes the effector element has been implanted at an implantation site that is farther than 1 cm from the nerve of the subject.

In an application, inhibiting the direct stimulation of the nerve includes inhibiting the direct stimulation of the nerve by driving the effector element after an implant that includes the effector element has been implanted at an implantation site that is farther than 2 cm from the nerve of the subject.

In an application, inhibiting the direct stimulation of the nerve includes inhibiting the direct stimulation of the nerve by driving the effector element after an implant that includes the effector element has been implanted at an implantation site that is farther than 3 cm from the nerve of the subject.

In an application, the effector element includes an electrode, and driving the effector element to apply the treatment includes driving a current through the electrode.

In an application, inhibiting the direct stimulation of the nerve includes configuring the current not to directly stimulate the nerve of the subject.

In an application, inhibiting the direct stimulation includes directing the current superficially.

In an application, the method further includes detecting movement of a limb of the subject in which the effector element has been implanted, and driving the effector element includes driving the effector element at least in part responsively to the detected movement.

In an application, detecting the movement includes detecting movement of the limb of the subject by detecting movement of an accelerometer that is coupled to the effector element.

In an application, detecting the movement of the limb of the subject includes detecting tremor of the limb of the subject.

In an application, driving the effector element at least in part responsively to the detected movement includes configuring the treatment at least in part responsively to the detected movement.

In an application, the movement of the limb has a frequency, and configuring the treatment includes configuring the treatment to have the frequency of the movement of the limb.

In an application, configuring the treatment includes configuring the treatment to be in phase with a phase of the movement of the limb.

In an application, configuring the treatment includes configuring the treatment to be out of phase with a phase of the movement of the limb.

There is further provided, in accordance with an application of the present invention, an implant, including:

a circuitry unit, configured to receive power wirelessly;

a lead, having a proximal end and a distal end, the proximal end configured to be coupled to the circuitry unit; and an array of microelectrodes, configured to be coupled to the circuitry unit by the lead, and configured to be coupled to a carotid sinus of a patient.

In an application, the microelectrodes are configured to contact one or more baroreceptors in the carotid sinus.

In an application, the circuitry unit is configured to drive the microelectrodes to deliver a current between 1 and 100 microamps.

In an application, the circuitry unit is configured to separately drive each microelectrode to apply a respective voltage.

There is further provided, in accordance with an application of the present invention, an implant, including:

a circuitry unit, configured to receive power wirelessly; and an array of microelectrodes, disposed on an outer surface of the circuitry unit.

The present invention will be more fully understood from the following detailed description of applications thereof, taken together with the drawings, in which:

BRIEF DESCRIPTION OF THE DRAWINGS

FIGS. 9A-B are schematic illustrations of another system for wireless neurostimulation, in accordance with respective applications of the present invention;

FIGS. 13A-B are schematic illustrations of implantation sites for implanting implants, in accordance with some applications of the invention;

FIGS. 14A-C are schematic illustrations of a system for asynchronous application of treatment using a plurality of implants, in accordance with some applications of the invention;

FIG. 15 is a schematic illustration of a system for asynchronous application of treatment using a plurality of implants, in accordance with some applications of the invention;

DETAILED DESCRIPTION OF APPLICATIONS

Figure 1:
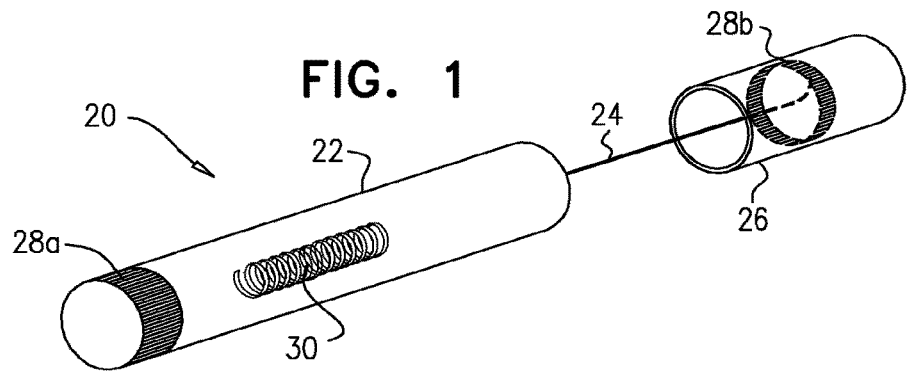
FIG. 1 is a schematic illustration of a system for wireless neurostimulation, in accordance with some applications of the present invention.

Reference is made to FIG. 1, which is a schematic illustration of medical implant 20, comprising a circuitry unit 22, and one or more effector elements, such as electrodes 28 (e.g., electrodes 28a and 28h), in accordance with some applications of the invention. At least one electrode (e.g., electrode 28b) is coupled to circuitry unit 22 via a lead 24. Typically, at least another electrode (e.g., electrode 28a) is disposed on a surface of the circuitry unit. Circuitry unit 22 is configured to drive a current through electrodes 28. For some applications of the invention, implant 20 further comprises a nerve cuff 26, e.g., as is known in the art, and the nerve cuff comprises the electrode that is coupled to the circuitry unit via the lead. For example, electrode 28b may be disposed on an inner surface of the nerve cuff.

For some applications of the invention, circuitry unit 22 comprises or is coupled to an antenna 30. Antenna 30 is illustrated as a coiled antenna purely as an example, but may take other forms, such as, but not limited to, those described with reference to FIGS. 17A-E. Antenna 30 is configured to receive data and/or power wirelessly from an external device, such as an extracorporeal device (e.g., a mattress-based transmitting unit, or a transmitting unit coupled to a belt, hat, eyeglasses, or clothing item of the patient) or another implant. For some applications, antenna 30 receives power wirelessly from an implanted transmitting unit coupled to a power supply (e.g., a battery). Alternatively or additionally, the circuitry unit receives power from a power supply (e.g., a battery), which may be in a common housing with the circuitry unit.

Circuitry unit 22 is typically small and tubular (e.g., 1-6 mm in diameter, and 5-50 mm in length), although the scope of the present invention includes other shapes for the circuitry unit (e.g., prismatic shapes, as described hereinbelow). For some applications, at least the circuitry unit itself is "injected" into a desired implantation site, using techniques known for implanting a BION™. For some applications, the entire implant is configured to be injectable. Similarly, except for differences noted herein, the circuitry unit typically comprises stimulation and/or sensing circuitry as is known for a BION™ or other tissue stimulation devices.

Figure 2:
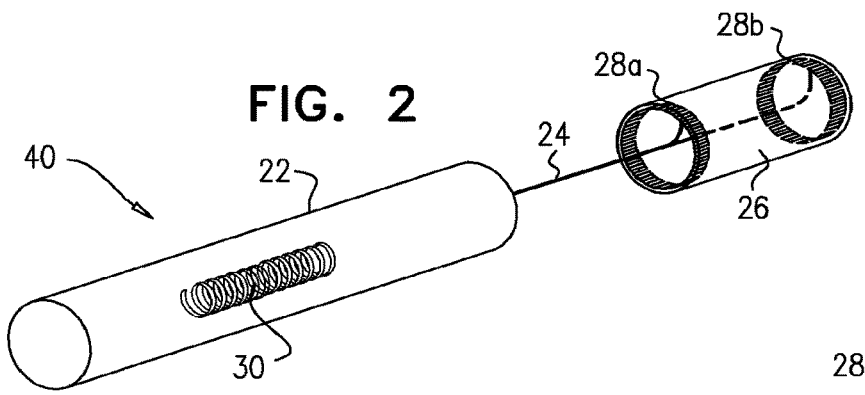
FIG. 2 is a schematic illustration of another system for wireless neurostimulation, in accordance with some applications of the present invention.

Reference is now made to FIG. 2, which is a schematic illustration of medical implant 40, comprising generally the same components as implant 20 shown in FIG. 1, except that both electrodes 28 (e.g., electrodes 28a and 28b) are coupled to circuitry unit 22 via lead 24, in accordance with some applications of the invention. For some applications, implant 40 comprises nerve cuff 26, and electrodes 28 are disposed on the nerve cuff, as described hereinabove.

Figure 3:
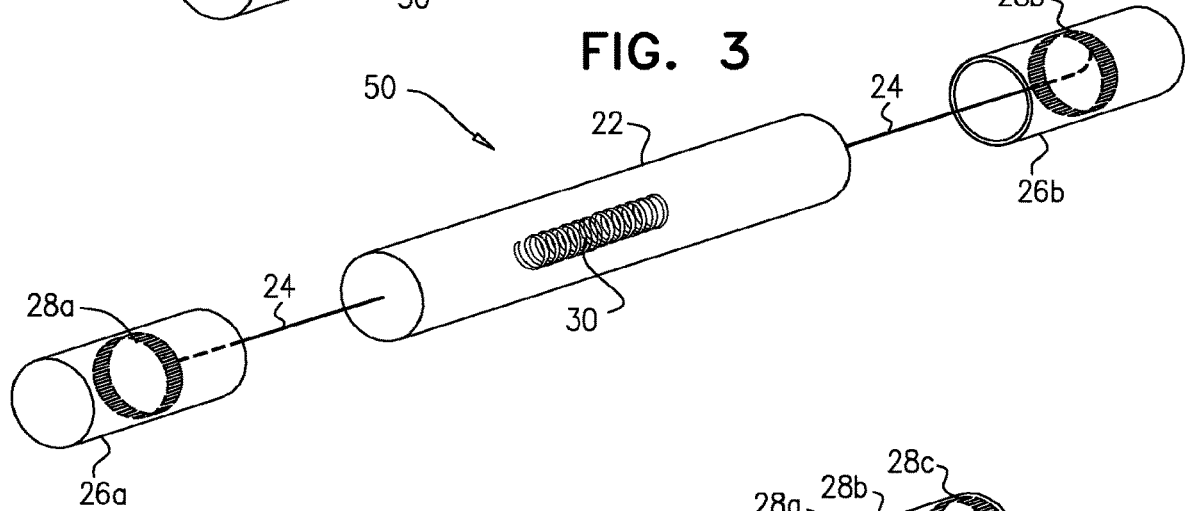
FIG. 3 is a schematic illustration of another system for wireless neurostimulation, in accordance with some applications of the present invention.

Reference is now made to FIG. 3, which is a schematic illustration of medical implant 50, comprising generally the same components as implant 40 shown in FIG. 2, except that electrodes 28 (e.g., electrodes 28a and 28b) are coupled to circuitry unit 22 via respective leads 24 (e.g., leads 24a and 24b), in accordance with some applications of the invention. For some applications, implant 50 comprises two or more nerve cuffs 26 (e.g., nerve cuffs 26a and 26b), and the electrodes are disposed on respective nerve cuffs.

Figure 4:
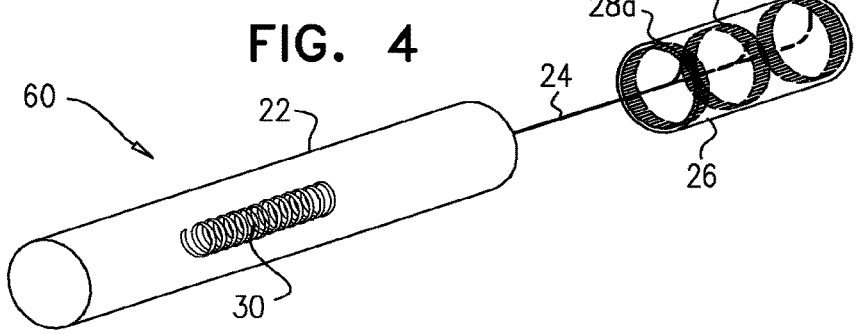
FIG. 4 is a schematic illustration of another system for wireless neurostimulation, in accordance with some applications of the present invention.

Reference is now made to FIG. 4, which is a schematic illustration of medical implant 60, comprising generally the same components as implant 20 shown in FIG. 1, except that the implant comprises a third electrode 28c, in accordance with some applications of the invention. For some applications, electrodes 28a, 28b and 28c are disposed on nerve cuff 26. For some applications of the invention, third electrode 28c is configured to facilitate unidirectional action potential propagation in the nerve. It is noted that, in accordance with some applications of the present invention, bidirectional stimulation is also possible using medical implant 60.

Figure 5:
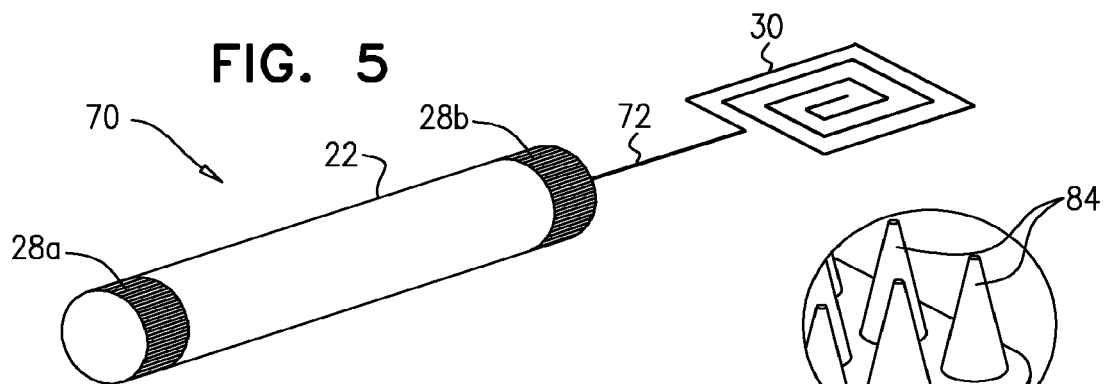
FIG. 5 is a schematic illustration of another system for wireless neurostimulation, in accordance with some applications of the present invention.

Reference is now made to FIG. 5, which is a schematic illustration of medical implant 70, comprising generally the same components as implant 20 shown in FIG. 1, except that both electrodes 28 are disposed on the outer surface of circuitry unit 22, and, rather than the circuitry unit comprising antenna 30, the antenna is disposed outside of the circuitry unit, and is coupled to the circuitry unit via a lead 72, in accordance with some applications of the invention. For some applications of the invention, antenna 30 may receive power and/or data, and/or may send sensing or diagnostic data acquired by circuitry unit 22 (e.g., data indicative of a state of the nerve of the patient). It is noted that although the circuitry unit of implant 70 is shown as having two electrodes on its outer surface, implant 70 may alternatively be configured as shown in other figures (e.g., FIGS. 1-4, 6-10C, or 11-12). For some such applications, the circuitry unit may in turn be coupled to one or more nerve cuffs or other implant for supporting electrodes in a suitable position for stimulating tissue.

Figure 6:
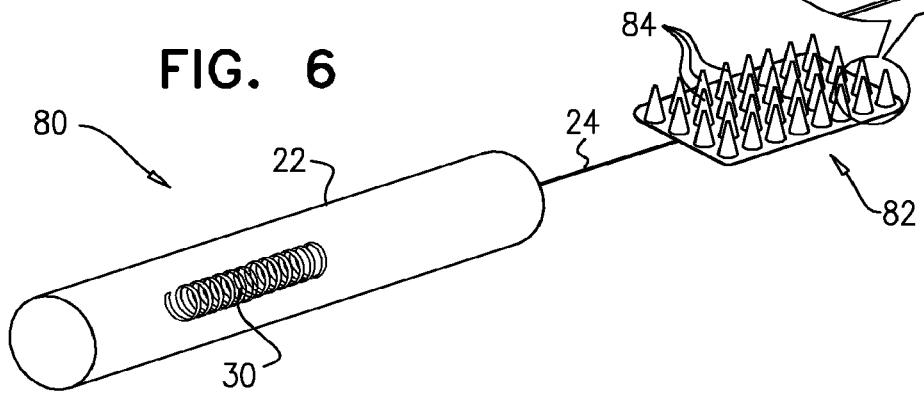
FIG. 6 is a schematic illustration of another system for wireless neurostimulation, in accordance with some applications of the present invention.

Reference is now made to FIG. 6, which is a schematic illustration of medical implant 80, comprising generally the same components as implant 20 shown in FIG. 1, except that circuitry unit 22 is coupled via lead 24 to a microelectrode array 82, comprising a plurality of microelectrodes 84, in accordance with an application of the present invention, in accordance with some applications of the invention. It is noted that the plurality of microelectrodes 84 are not drawn to scale. For some applications, microelectrode array 82 is flexible, in order to more closely conform to the shape of a tissue into which the microelectrodes penetrate. For example, array 82 may be placed generally flat against a large structure (e.g., the heart or a portion of the gastrointestinal tract) or a large-diameter structure (e.g., the spinal cord), or array 82 may be at least partially (e.g., completely) wrapped around a structure, such as a nerve or a blood vessel.

According to some applications of the present invention, microelectrode array 82 may be coupled to a carotid sinus of the patient, and more specifically to baroreceptors in the carotid sinus. According to one application of the present invention, each microelectrode 84 is individually controllable by circuitry unit 22, thereby facilitating a calibration period in which the effect of current from each microelectrode on baroreceptor activity and/or blood pressure may be assessed, and in which a stimulation protocol for each microelectrode may be created. For example, each microelectrode may be individually coupled to circuitry unit 22, or may be coupled to the circuitry unit via a multiplexer.

For some applications of the invention, the techniques described for use with implant 80 and/or microelectrode array 82 may be combined with other implants described herein. For example, each microelectrode of the microelectrode array of implant 90, described with reference to FIG. 7, may be individually controllable, as described for the microelectrodes of implant 80, mutatis mutandis. Alternatively or additionally, one or more other implants described herein may be configured and/or implanted to stimulate baroreceptors of a subject, such as baroreceptors of the carotid artery of the subject.

According to some applications of the present invention, microelectrodes 84 each deliver a current that is less than 1000 microamps, e.g., 10-100 microamps, or 1-10 microamps.

Figure 7:
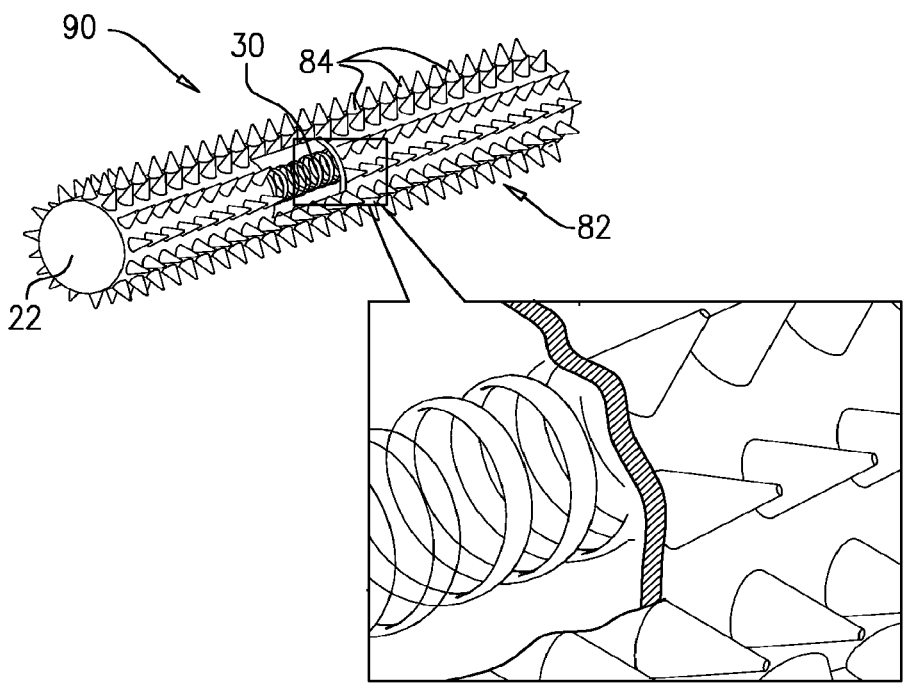
FIG. 7 is a schematic illustration of another system for wireless neurostimulation, in accordance with some applications of the present invention.

Reference is now made to FIG. 7, which is a schematic illustration showing a cross-section of medical implant 90, comprising generally the same components as implant 80 shown in FIG. 6, except that at least one microelectrode array 82, comprising microelectrodes 84, is disposed on the outer surface of circuitry unit 22, in accordance with some applications of the invention. It is again noted that microelectrodes 84 are not drawn to scale.

Figure 8A:
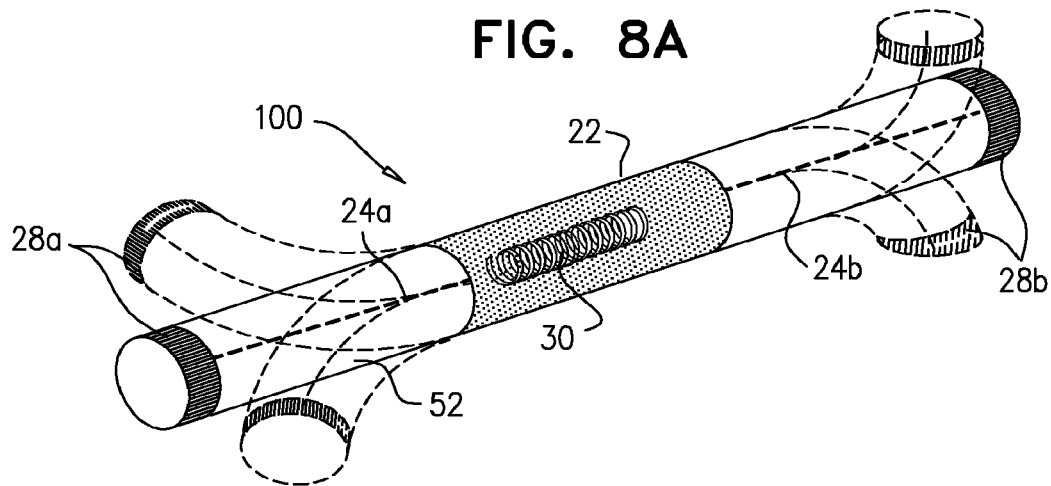
FIGS. 8A-C are schematic illustrations of another system for wireless neurostimulation, in accordance with some applications of the present invention.
Figure 8B:
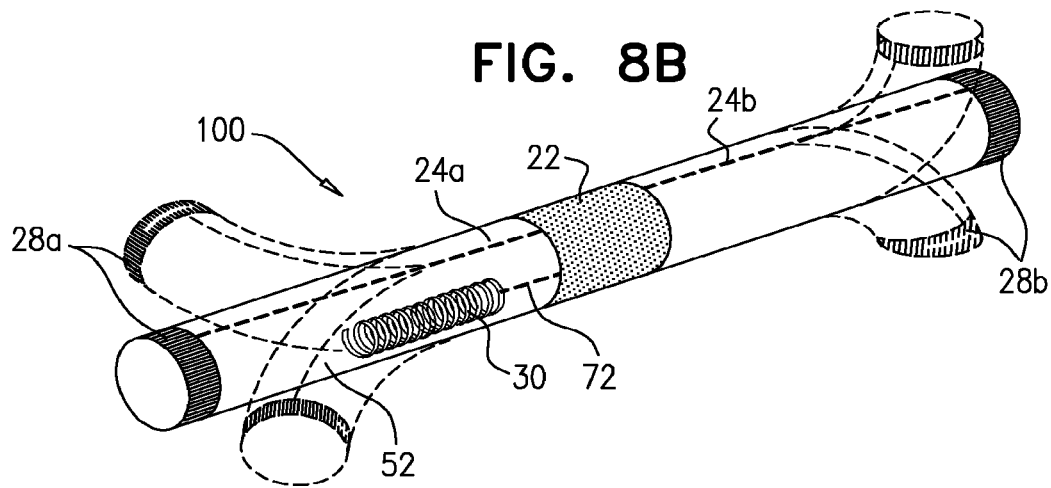
Figure 8C:
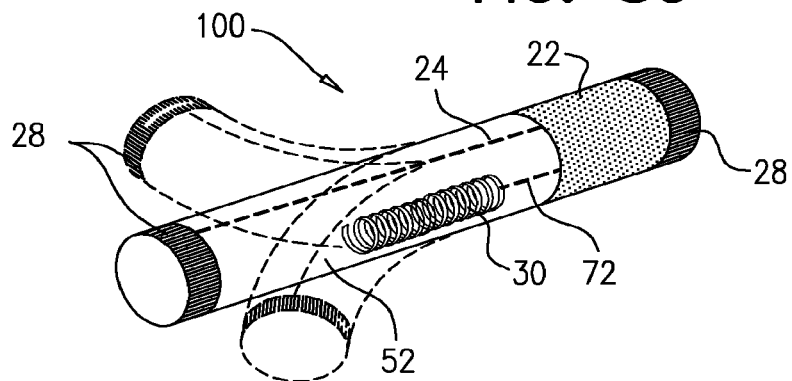

Reference is now made to FIGS. 8A-C, which are schematic illustrations of medical implant 100, comprising circuitry unit 22, electrodes 28, and a flexible tubular element 52, in accordance with respective applications of the invention. For some applications of the invention, implant 100 is analogous to medical implant described hereinabove, such as implant 20. Tubular element 52 typically comprises flexible silicone. Circuitry unit 22 is typically disposed inside tubular element 52, and at least part of each electrode 28 is exposed at an outer surface of element 52. For some applications, electrodes 28 are disposed on the outside of element 52. Leads 24 electrically couple respective electrodes 28 to circuitry unit 22, and are typically disposed within element 52. Typically, implant 100 is injectable (e.g., percutaneously injectable), as described hereinabove.

For some applications of the invention, and as shown in FIG. 8A, circuitry unit 22 comprises antenna 30 (e.g., as described with reference to FIG. 1). For some applications of the invention, and as shown in FIG. 8B, antenna is disposed outside of the circuitry unit, and is coupled to the circuitry unit via lead 72 (e.g., as described with reference to FIG. 5). FIGS. 8A-B show circuitry unit 22 being disposed generally midway along the length of tubular element 52. However, other configurations may be used. For example, and as shown in FIG. 8C, circuitry unit 22 may be disposed at one end of element 52, and/or an electrode 28 may be disposed on the outer surface of the circuitry unit.

For applications of the invention in which circuitry unit 22 is disposed within flexible tubular casing 52 (e.g., as described with reference to FIGS. 8A-C, and 10C), the circuitry unit typically comprises a hermetically-sealed casing, such as a ceramic or glass casing.

Reference is again made to FIGS. 1-6 and 8A-C. Circuitry unit 22 comprises circuitry, such as an application-specific integrated circuit (ASIC), and is typically (e.g., necessarily) rigid. Typically, each implant described with reference to FIGS. 1-6 and 8A-C (e.g., implants 20, 40, 50, 60, 70, 80, and/or 100) is configured such that at least two of the components of the implant are flexibly coupled to each other. For example, electrodes 28 and/or antenna 30 may be flexibly coupled to circuitry unit 22. Leads 24 and 72, and tubular element 52 are typically flexible, and typically provide such flexible coupling. For some applications, at least one component that would otherwise be disposed in or on an injectable stimulatory implant, such as a BION™ (e.g., an antenna and/or an electrode), is disposed outside of circuitry unit 22. For some such applications, this configuration thereby facilitates the miniaturization of circuitry unit 22, e.g., such that circuitry unit 22 is smaller than a BION™. For some applications, at least one component that would otherwise be rigidly coupled to a circuitry unit of an injectable stimulatory implant, such as a BION™, is, in the present invention, flexibly coupled to circuitry unit 22. It is hypothesized that this flexible coupling and/or this miniaturization of circuitry unit 22, facilitates maintenance of contact between the electrodes and the tissue into which the current is being driven and/or increases versatility of the implant, e.g., by facilitating placement of the implant in positions in which a fully-rigid implant is not placeable.

Figure 9B:
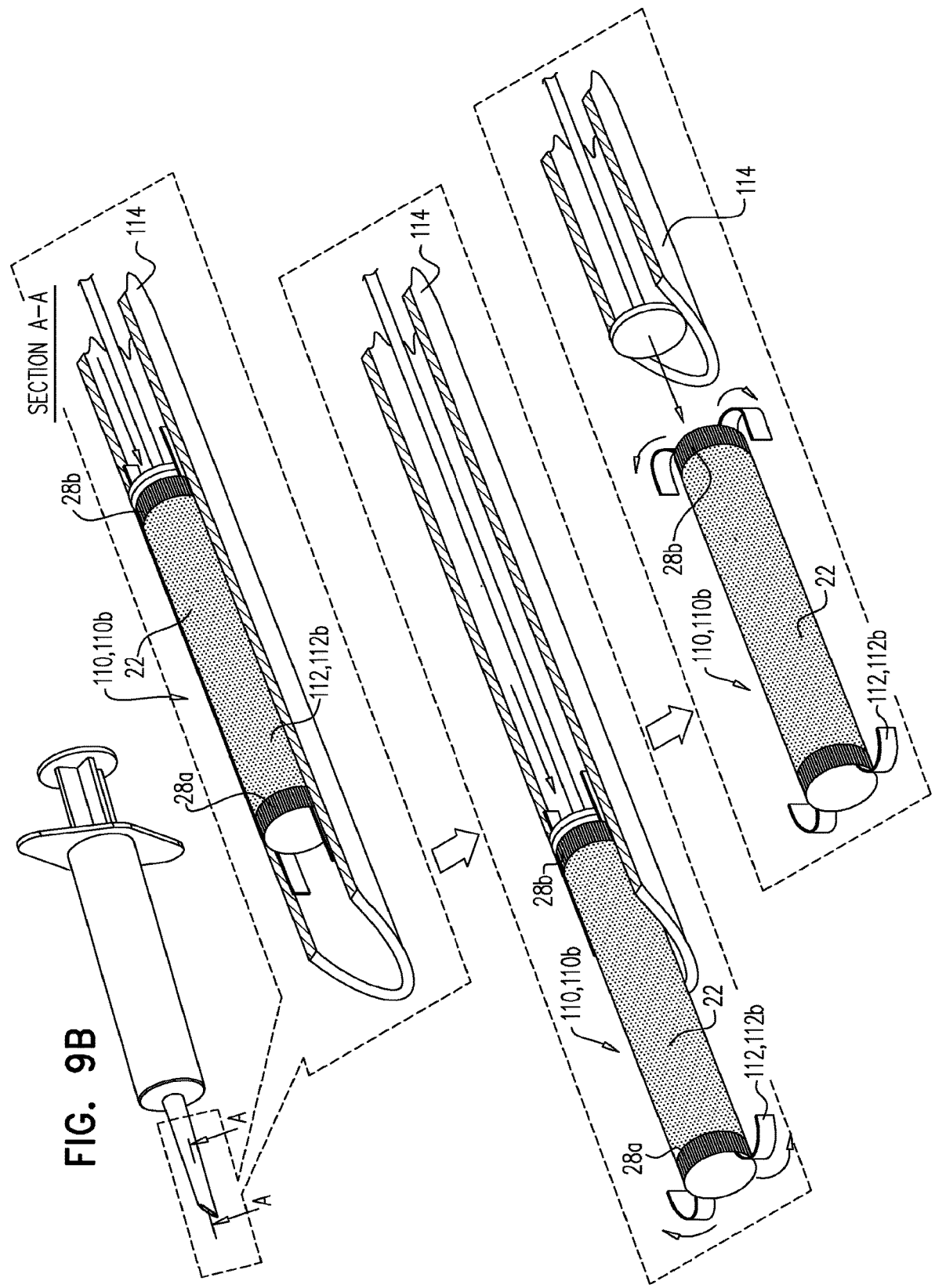

Reference is made to FIGS. 9A-B, which are schematic illustrations of medical implant 110, and steps in the implantation thereof, in accordance with respective applications of the invention. Implant 110 comprises circuitry unit 22, one or more electrodes 28 (e.g., electrodes 28a and 28b), and one or more anchors 112. For some applications of the invention, implant 110 is analogous to medical implant described hereinabove, such as implant 20. FIG. 9A shows implant 110 embodied as implant 110a, comprising anchors 112, embodied as anchors 112a. FIG. 9B shows implant 110 embodied as implant 110b, comprising anchors 112, embodied as anchors 112b.

Anchors 112 are configured to inhibit movement of implant 110, following delivery of the implant to the desired implantation site. Implant 110 is typically "injected" into the desired implantation site, e.g., using techniques known for implanting a BION™. Typically, anchors 112 have (1) a delivery configuration, in which the anchors are configured to fit within, and be slidable through, a lumen of a delivery device 114, such as a hollow needle, and (2) an anchoring configuration in which the anchors protrude laterally and/or radially from the body of implant 110 (e.g., from circuitry unit 22), and into tissue at the implantation site. As shown in step (1) of FIG. 9A, anchors 112a, in the delivery configuration thereof, are disposed against the body of implant 110 (e.g., against circuitry unit 22).

As shown in step (1) of FIG. 9B, anchors 112b, in the delivery configuration thereof, are typically generally straight, and are disposed proximally and/or distally from the body of implant 110 (e.g., from circuitry unit 22). That is, in the delivery configuration, anchors 112 generally do not inhibit movement of implant 110 along a longitudinal axis thereof, and in the anchoring configuration, the anchors generally do inhibit such movement. Typically, anchors 112 are configured to be biased toward assuming the anchoring configuration, and are constrained in the delivery configuration by delivery device 114, e.g., as shown in FIG. 9A. As implant 110 is exposed from delivery device 114, anchors 112 automatically move toward the anchoring configuration, e.g., as shown in steps (2) and (3) of FIGS. 9A and 9B. Typically, anchors 112 are thus configured by comprising a shape-memory material that is shape-set in the anchoring configuration. Non-limiting examples of materials that anchors 112 may comprise include nickel-titanium (Nitinol), stainless steel, nickel cobalt, cobalt chrome, titanium, tantalum, and palladium.

As shown in steps (2) and (3) of FIG. 9A and FIG. 9B, movement of anchors 112 toward the anchoring configuration thereof comprises rotation (e.g., deflection) of the anchors around a coupling point of the anchors to circuitry unit 22, and/or bending of the anchors, such that at least a portion of each anchor protrudes laterally and/or radially from circuitry unit 22.

Although FIGS. 9A-B show implant 110 (e.g., implants 110a and 110b) comprising 2 anchors 112 at each end of the implant, the scope of the invention includes other numbers and/or arrangements of anchors. For example, implant 110 may comprise 3 or more anchors 112 at each end of the implant, or may comprise anchors only at one end of the implant.

It is to be noted that anchors 112 (e.g., anchors 112a and 112b) are shown and described with reference to FIGS. 9A-B as illustrative examples, and the scope of the invention includes other embodiments of anchors 112.

It is to be noted that the configuration of the circuitry unit and electrodes of implant 110 shown in FIGS. 9A-B is for illustration, and the circuitry unit and electrodes of implant 110 may alternatively be configured as shown in other figures (e.g., FIGS. 1-8C, 10A-C, or 11-12). Similarly, anchors 112 may be used in combination with other medical implant described herein (e.g., with the circuitry units, electrodes, antennae, and/or tubular elements thereof).

Figure 10A:
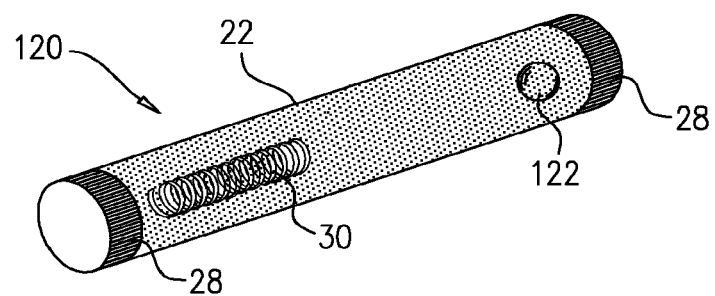
FIGS. 10A-C are schematic illustrations of another system for wireless neurostimulation, in accordance with some applications of the present invention.
Figure 10B:
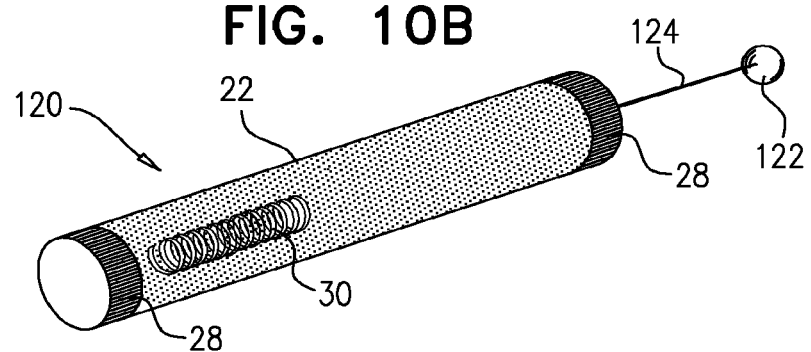
Figure 10C:
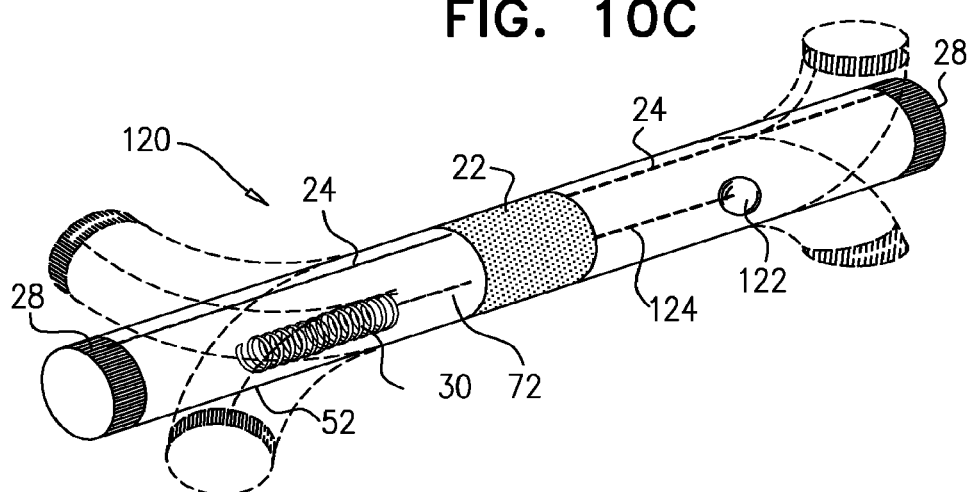

Reference is made to FIGS. 10A-C, which are schematic illustrations of medical implant 120, comprising circuitry unit 22, electrodes 28, and an accelerometer 122, in accordance with respective applications of the invention. For some applications of the invention, implant 120 is analogous to medical implant described hereinabove, such as implant 20. Accelerometer 122 is configured to sense movement of the site at which implant 120 is implanted, and to responsively provide a signal to circuitry unit 22. For example, when implant 120 is used to treat a movement disorder, accelerometer 122 may be used to sense incidents of, and/or improvement in, the disorder, e.g., as described hereinbelow with reference to FIGS. 13A-B. Similarly, accelerometer 122 may be used to sense when the subject is at a specific level of activity (e.g., at rest) and/or in a specific position (e.g., lying down or standing up), and circuitry unit 22 is configured to drive the current in response to the sensed activity level and/or position.

FIG. 10A shows an application of the invention in which accelerometer 122 is disposed within circuitry unit 22. FIG. 10B shows an application of the invention in which accelerometer 122 is disposed outside of circuitry unit 22, and is coupled to the circuitry unit via a lead 124. FIG. 10C shows an application of the invention in which accelerometer 122 is disposed outside of circuitry unit 22, is coupled to the circuitry unit via lead 124, and is disposed within tubular element 52. Although FIGS. 10A-C show specific examples of applications of the invention in which the medical implant comprises accelerometer 122, the use of accelerometer 122 may be combined with other medical implant described herein (e.g., may be coupled to other circuitry units described herein).

For some applications of the invention, an extracorporeal device, e.g., a worn extracorporeal device, such as a wristwatch-based device may alternatively or additionally comprise an accelerometer, and transmit wireless power in response to a detected movement, activity level, and/or position.

Figure 12:
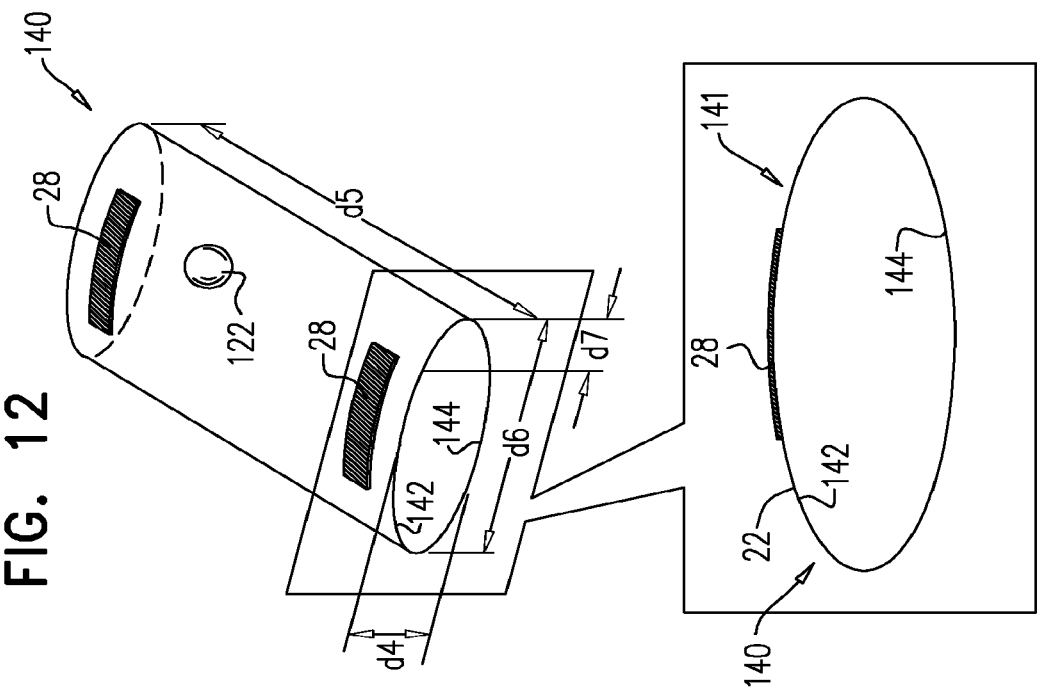
FIG. 12 is a schematic illustration of another system for wireless neurostimulation, in accordance with some applications of the present invention.
Figure 11:
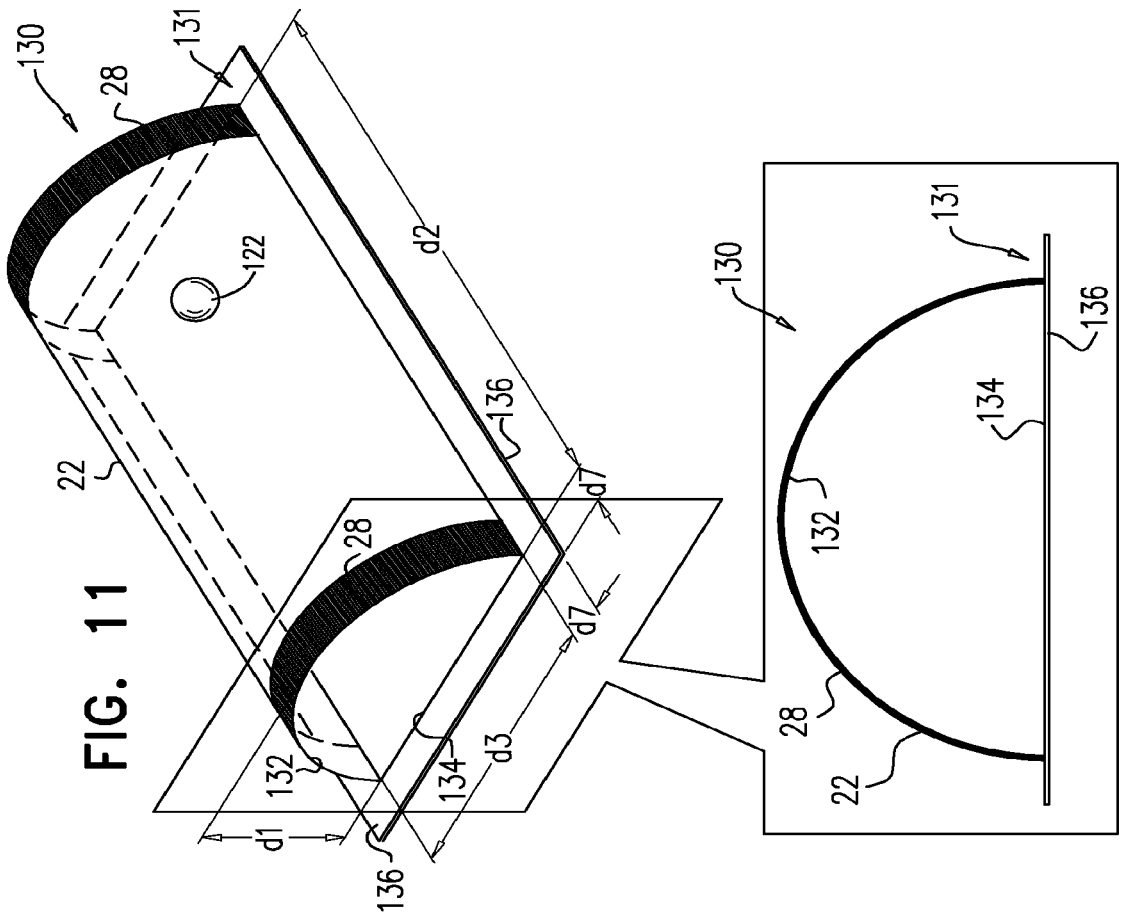
FIG. 11 is a schematic illustration of another system for wireless neurostimulation, in accordance with some applications of the present invention.

Reference is made to FIGS. 11 and 12, which are schematic illustrations of medical implant 130 and 140, respectively, comprising circuitry unit 22, and electrodes 28. Implants 130 and 140 are typically configured to be implanted intradermally or subcutaneously. That is, implants 130 and 140 are typically configured to be placed deeper than a surface of the skin of the subject (e.g., deeper than the epidermis). Implants 130 and 140 are further typically configured to be implanted by "injecting" (e.g., as described hereinabove for other implants, mutatis mutandis). Typically, implant 130 and 140 are shaped to define respective prismatic shapes, having a skin-facing side, and an opposing side. Implant 130 is typically shaped to define a prism that has a transverse cross-section that has a generally arced upper portion 132 that defines the skin-facing side of the implant, and a generally flat lower portion 134 that defines the opposing side of the implant. For example, the transverse cross-section of implant 130 may be generally semicircular. Implant 140 has a transverse cross-section that is generally elliptical, having a generally arced upper portion 142 that defines the skin-facing side of the implant, and a generally arced lower portion 144 that defines the opposing side of the implant. Implants 130 and 140 are typically shaped such that a height d1 and d4, respectively, from the skin-facing side to the opposing side, is smaller than both (1) a longest length d2 and d5, respectively, and (2) a width d3 and d6, respectively, of the implant. That is, compared to a generally cylindrical implant, implant 130 and 140 have generally flattened configurations (i.e., a "low profile").

Typically, dimension d1 is greater than 0.5 mm and/or less than 3 mm (e.g., about 1.5 mm). Typically dimension d4 is greater than 0.5 mm and/or less than 3 mm (e.g., between 1.5 and 2 mm). Typically, dimensions d2 and d5 are greater than 5 mm and/or less than 30 mm (e.g., between 10 and 30 mm, such as between 10 and 20 mm). Typically, dimensions d3 and d6 are greater than 1 mm and/or less than 5 mm (e.g., between 1.5 and 3 mm).

The shapes of implant 130 and 140 are given as non-limiting examples of flattened configurations; other shapes may also be used. For example, implant 130 and/or 140 may be generally flat (e.g., sheet-like), having electrodes 28 disposed on one side. When the implant is flat, the implant typically comprises a resilient material, and is configured to remain generally flat or slightly curved (e.g., not to curl up). Furthermore, other medical implant and/or circuitry units described herein may also be configured to have a flattened configuration for intradermal and/or subcutaneous implantation.

Typically, electrodes 28 of implant 130 and 140 are disposed generally on one side of the implant. For example, electrodes 28 of implant 130 are typically disposed only on upper portion 132, and electrodes 28 of implant 140 are typically disposed only on upper portion 142. Thereby, implants 130 and 140 typically have a conducting side (i.e., the side on which the electrodes are disposed). This configuration is hypothesized to direct the current that is driven through electrodes 28 by circuitry unit 22, to tissue at the conducting side of the implant (e.g., to tissue adjacent to the upper portion of the implant). That is, implants 130 and 140 are typically directional. Typically, the skin-facing side of the implant defines the conducting side of the implant.

For some applications of the invention, and as shown for implant 130, the implant may comprise an inhibiting element, such as an insulating member 136, (e.g., an insulating layer), configured to inhibit electrical conduction therethrough. Typically, insulating member 136 is disposed on, such as coupled to, the lower portion and/or the opposing side of the implant, so as to inhibit electrical conduction from electrodes 28 into tissue adjacent to the lower portion of the implant, i.e., into tissue at the opposing side of the implant. Thereby, insulating member 136 contributes toward the one-sided configuration of the implant. Although insulating member 136 is shown as a component of implant 130, the insulating member may be used to facilitate the one-sidedness of medical implant 140. Element 136 may also be used in combination with other medical implant described herein. For example, one or more elements 136 may be (1) disposed around at least part of nerve cuff 26, so as to inhibit conduction of current away from a nerve around which the cuff is disposed, or (2) disposed around at least part of a circuitry unit and/or tubular element, so as to provide one-sidedness thereto. Insulating member 136 may comprise any suitable material known in the art, such as insulating silicone.

For some applications of the invention in which the implant comprises an insulating member, electrodes 28 laterally circumscribe the implant, and part of the electrodes is covered by the insulating member. That is, for some applications of the invention, electrodes 28 are not disposed generally on one side of the implant. For example, electrodes 28 of implant 130 may be disposed circumferentially around circuitry unit 22, and part of the electrodes is sandwiched between the circuitry unit and insulating member 136. For some such applications, this configuration facilitates manufacturing of the implant, e.g., by facilitating the application of the electrodes to the surface of the circuitry unit.

Implants 130 and 140 are thereby typically directional, having a conducting skin-facing side and, for some applications, an insulating member at the lower portion of the implant, which provides an insulating opposing side of the implant. Typically, electrodes 28 of implants 130 and 140 are disposed at least 1 mm (e.g., greater than 2 mm, such as greater than 5 mm) from the lateral edges of the implant.

That is, the implants typically define respective lateral zones 131 and 141, on the skin-facing side of the implants, the lateral zones having a width of distance d7, in which electrodes 28 are not disposed, distance d7 being greater than 1 mm (e.g., greater than 2 mm, such as greater than 5 mm). For example, the lateral zone may include the insulating member (as shown in FIG. 11 for lateral zone 131 of implant 130) and/or a portion of the upper portion of the circuitry unit on which electrodes are not disposed (e.g., as shown in FIG. 12 for lateral zone 141 of implant 140). It is hypothesized that providing the lateral zone in which electrodes 28 are not disposed, facilitates the one-sidedness of the implant, by inhibiting electrical conduction from electrodes 28 into tissue adjacent to the lower portion of the implant, i.e., into tissue at the opposing side of the implant.

For some applications of the invention, implants 130 and 140 define lateral zones 131 and 141 on the opposing side of the implant, and are configured to be implanted such that the electrodes of the implant face away from the skin. Thereby, for such applications, implants 130 and 140 are configured to inhibit electrical conduction from the electrodes into the skin that is superficial to the implant, e.g., so as to stimulate underlying muscle and or nerves. It is hypothesized that, for such applications, current applied from electrodes 28 advantageously induces less pain in the subject than does current from external skin-mounted electrodes (e.g., Transcutaneous Electrical Nerve Stimulation electrodes), e.g., due to reduced stimulation of sensory nerve fibers.

Typically, implants 130 and 140 further comprise accelerometer 122, described hereinabove with reference to FIGS. 10A-C. Alternatively, implants 130 and 140 may be used in combination with a an extracorporeal device that comprises an accelerometer.

Reference is again made to FIGS. 1-12. Typically, at least the circuitry units of the respective implants described hereinabove are configured to be "injectable" (e.g., percutaneously deliverable via a hollow needle, and/or using techniques known for implanting a BION™). For some applications, the entire implant is configured to be injectable.

For some applications, the implants described with reference to FIGS. 1-12 are wirelessly powered by a transmitting device, e.g., via radio-frequency (RF) or electromagnetic induction, such as described hereinbelow with reference to FIGS. 14A-C, mutatis mutandis.

For such applications, the implants typically do not comprise a power supply such as a battery. For clarity, throughout this patent application, including the claims, a "power supply" is defined as an element that is configured to continuously power the implant for a period of greater than one minute. For some applications, the implants described with reference to FIGS. 1-12 comprise a temporary power storage element (e.g., to facilitate a delay between receiving wireless power and applying a treatment). For clarity, throughout this patent application, including the claims, a "temporary power storage element" is defined as an element that is configured to continuously power the implant for a period of up to one minute. For some applications of the invention, the implants are passive implants, and operate only while wireless power is received (e.g., the implants do not comprise a power supply or a temporary power storage element, and consume power as it is received). For some such applications, the transmitting device is worn by the subject, and/or is disposed in, on, or under, an item of furniture or clothing of the subject, such as a bed or a hat of the subject.

Alternatively, the implants described with reference to FIGS. 1-12 may comprise a power supply (i.e., a power supply that is configured to continuously power the implant for a period of greater than one minute). For example, the implants may comprise a battery that is configured to continuously power the implant for a period of up to three days, and to be wirelessly charged once per day (e.g., at night). Alternatively, the implants may comprise a battery that is configured to power the implant for more than three days (e.g., for more than a month, such as for more than a year).

Figure 13B:
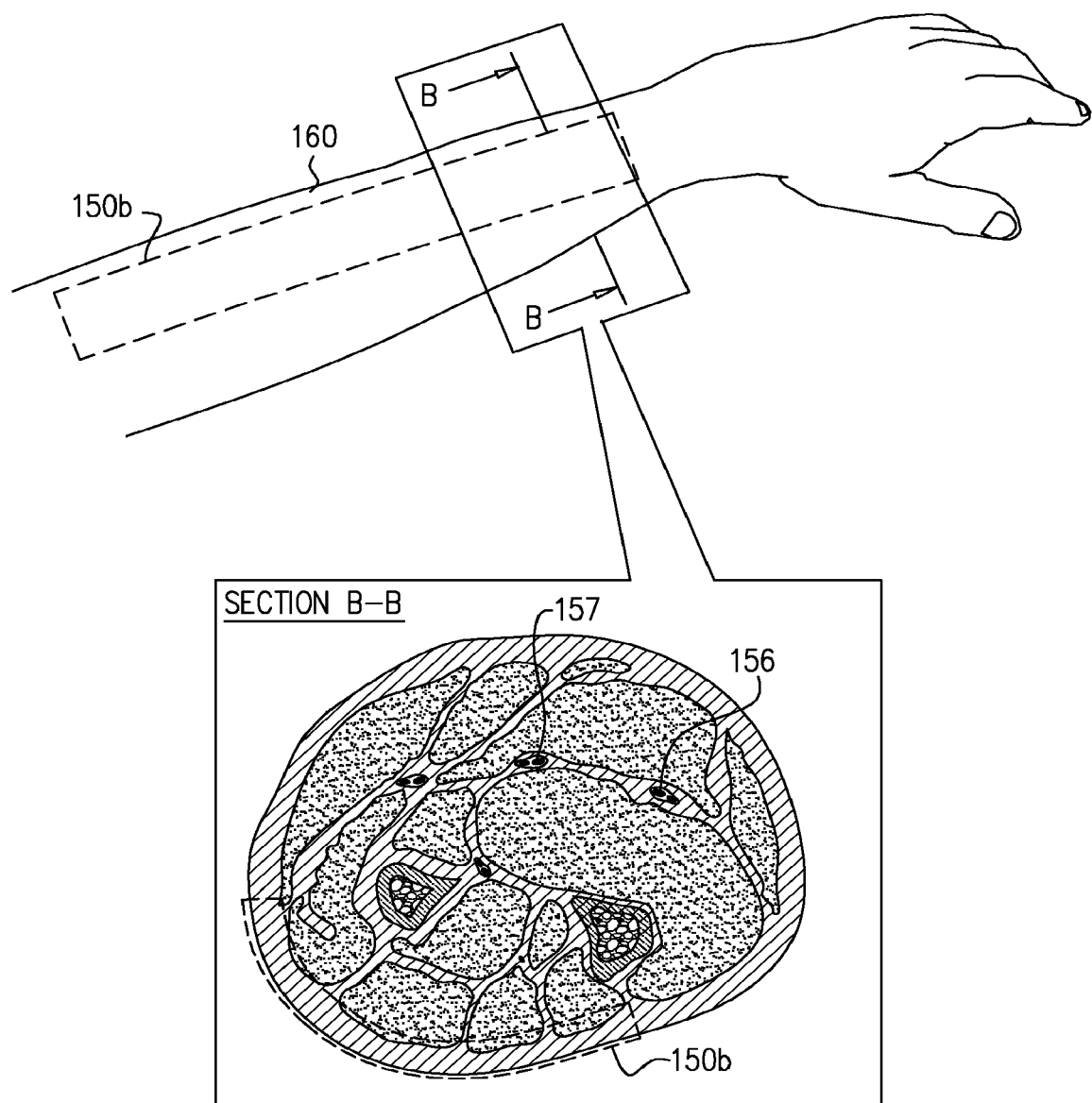

Reference is made to FIGS. 13A-B, which are schematic illustrations of medical implant 130, having been implanted at respective implantation sites 150 (e.g., implantation sites 150*a* and 150*b*) in an arm 160 of a subject, so as to treat tremor of at least the arm of the subject, in accordance with some applications of the invention. In FIGS. 13A-B, medical implant 130 is shown as an example of such an implanted medical implant, but it is to be noted that the scope of the invention includes the implantation, at the implantation sites, of other medical implants, such as those described herein, mutatis mutandis. Similarly, the techniques described herein may also be used to treat tremor at another site in the body of the subject, such as in another limb of the subject, such as in a leg of the subject.

Implantation sites 150 (e.g., implantation site 150*a* and implantation site 150*b*) are intradermal or subcutaneous. Typically, implant 130 is implanted within subcutaneous tissue of a subject, and is typically delivered by injection (e.g., using techniques known for implanting a BION™, and/or as described with reference to FIGS. 9A-B, mutatis mutandis). Subcutaneously- and intradermally-implanted implants typically distend overlying skin and/or compress underlying tissue, due to the volume and/or shape of the implant. As described hereinabove, implant 130 is shaped to have a low profile, compared to a similar cylindrical implant. Thereby, when implanted subcutaneously, implant 130 distends overlying skin 152 and/or compresses underlying tissue, such as muscle 154, less than does an implant with a greater profile (e.g., a cylindrical implant). Typically, implant 130 is implanted such that upper portion 132 faces the skin, and lower portion 134 faces the underlying tissue, thereby positioning electrodes 28 toward the skin and, if the implant includes insulating member 136, positioning the insulating member toward the underlying tissue. That is, when implanted subcutaneously, the conducting side of the implant is typically a skin-facing side of the implant. Implanting implant 130 in this configuration thereby configures the implant to direct current toward the skin and/or away from the underlying tissue.

Circuitry unit 22 is typically configured to drive a current through electrodes 28, and to configure the current to stimulate sensory fibers in the skin of the subject. Typically, the subject thereby feels the current being delivered (i.e., the implant induces a sensation in the skin of the subject). For some applications, the current may induce at least temporary discomfort or even pain in the subject, and, for some applications, this is desirable for successful treatment. For some applications, the current may be configured to have an amplitude that is great as possible without causing pain. For some applications, the current and/or sensations induced by the current may be similar to those of TENS apparatus, as is known in the art. Typically, circuitry unit 22 configures the current to a frequency of greater than 1 and/or less than 150 Hz, but other frequencies may also be used.

It is hypothesized that stimulation of sensory fibers in the skin of the limb of the subject (e.g., as described in the above paragraph) reduces the intensity and/or frequency of tremor in at least that limb. Typically, the stimulation of the sensory fibers in the skin is performed predominantly without directly stimulating underlying tissue such as underlying muscles and/or nerves (i.e., muscles and/or nerves that are disposed deeper than the implant). That is, action potentials are predominantly initiated in sensory fibers in the skin, i.e., upstream of nerves. (In this application, the term "nerve" is intended to be distinct from the term "sensory fiber".) For example, the implant is typically configured so as to predominantly not (1) directly initiate action potentials in nerves, such as ulnar nerve 156, (2) stimulate sensory fibers in underlying muscle, and/or (3) induce contraction of underlying muscle (e.g., spasm).

For some applications of the invention, the implant is configured to perform this selective stimulation of sensory fibers by the implant being directional, e.g., as described with reference to FIGS. 11-12. For such applications, the implant is typically implanted such that the conducting side of the implant (e.g., the side on which electrodes are disposed) faces superficially, thereby directing the current superficially (e.g., toward the skin). Similarly, implants comprising an insulating member are typically implanted such that the insulating member is disposed deeper into the subject than the electrodes. That is, for such applications, the electrodes are typically disposed on a superficial side (e.g., a skin-facing side) of the implant, and/or the insulating member is typically disposed on a deep side of the implant. Thereby, insulating member 136 and/or lateral zones 131 and 141 act as inhibiting elements that inhibit direct stimulation of one or more nerves disposed deeper than the implanted implant.

For some applications of the invention, the implant is configured to perform the selective stimulation of sensory fibers in the skin, by circuitry unit 22 being configured to configure the current that it drives via electrodes 28, to selectively stimulate the sensory fibers in the skin. For example, circuitry unit 22 may configure the current to have an amplitude that is sufficient to stimulate the sensory fibers in the skin but insufficient to initiate action potentials in sensory fibers in muscle and/or nerves, and/or to induce contraction of muscle. Alternatively or additionally, circuitry unit 22 may configure the current to have another characteristic, such as a frequency, a pulse width, and/or an on-off pattern (i.e., durations for which the wireless power is transmitted and not transmitted) that facilitates such selective stimulation of sensory fibers in the skin.

For some applications, the electrodes of the implant are disposed close to each other (e.g., less than 10 mm from each other, such as less than 2 mm from each other), so as to inhibiting the current that flows between the electrodes, from flowing far from the implant, and thereby inhibiting the current that flows between the electrodes from reaching the nerves disposed deeper than the implanted implant.

For some applications of the invention, the implant is configured to perform the selective stimulation of sensory fibers in the skin by being implanted sufficiently close to the sensory fibers in the skin, and sufficiently far from the underlying muscle and/or nerves. For example, and as shown in FIG. 13B, the implant may be subcutaneously implanted at implantation site 150b, on the lateral side (i.e., the "back") of the forearm, which is generally farther from ulnar nerve 156 and median nerve 157, than are sites on the medial side (i.e., the "inside") of the forearm. For example, implantation site 150b may be farther than 1 cm (e.g., farther than 2 cm, such as farther than 3 cm) from the ulnar nerve and/or the median nerve.

For some applications, and as shown in FIG. 13A, the implant may be otherwise sufficiently configured to perform the selective stimulation of sensory fibers (e.g., as described hereinabove), such that it is possible to implant the implant at an implantation site, such as implantation site 150a, that is closer to nerves, such as nerves 156 and 157, predominantly without stimulating the nerves. For some applications of the invention, it may be even be desirable to implant the implant at such a site, e.g., so as to facilitate stimulation of specific sensory fibers that conduct impulses toward one or more specific nerves.

As described hereinabove, implant 130 typically comprises accelerometer 122, which is configured to sense movement of the implantation site, and to responsively provide a signal to circuitry unit 22. Accelerometer 122 is typically configured to sense tremor of the limb, and circuitry unit 22 is typically configured to drive the current via electrodes 28 at least in part responsively to the sensed tremor. The circuitry unit may be configured to apply the current in phase or out of phase with the tremor. For example, circuitry unit 22 may be configured to drive the current only during particular phases of the tremor (e.g., during a highest speed portion of the tremor, or, alternatively, only when the limb is at one or both of the endpoints of its tremor-induced travel). That is, the circuitry unit may be configured to modulate the current onto the tremor. Alternatively or additionally, the circuitry unit may be configured to change one or more parameters of the current during particular phases of the tremor.

For some applications of the invention, accelerometer 122 is used to adjust timing (e.g., phasing) and/or other parameters of the current, so as to optimize treatment of the tremor. For example, circuitry unit 22 may automatically adjust the phase(s) of the tremor during which it drives the current (i.e., the "angle of phase" at which it drives the current), until optimal treatment is achieved, e.g., by "sweeping" different angles of phase. Similarly, other current parameters, such as frequency and amplitude, may be optimized automatically by circuitry unit 22.

For some applications of the invention, an extracorporeal device, e.g., a worn extracorporeal device, comprises an accelerometer, and is configured and/or positioned to detect the tremor, and circuitry unit 22 of the implant is configured to drive the current in response to the extracorporeal device detecting the tremor. For example, a wristwatch-based extracorporeal device may be worn on an arm of the subject. The wristwatch-based extracorporeal device comprises an accelerometer and, in response to detecting the tremor in the arm of the subject, transmits wireless power. The implant receives the wireless power and, in response to the wireless power (e.g., powered by the wireless power), drives the current into the arm of the subject (e.g., into the skin thereof). For such applications, the implant typically does not comprise a power supply. For applications in which a worn extracorporeal device comprises an accelerometer, the implant typically does not comprise an accelerometer.

For some applications, circuitry unit 22 is configurable (e.g., manually configurable) using an extracorporeal device, such that an operator may adjust parameters such as phase angle, frequency and amplitude of the current.

For some applications of the invention, tremor in one limb may be treated by an implant implanted in a contralateral limb. For example, tremor in only one limb may be treated by an implant implanted in a contralateral limb, or tremor in a pair of limbs may be treated by an implant implanted in only one of the pair of limbs (i.e., a limb that is contralateral to at least one of the limbs that experiences the tremor).

Figure 14A:
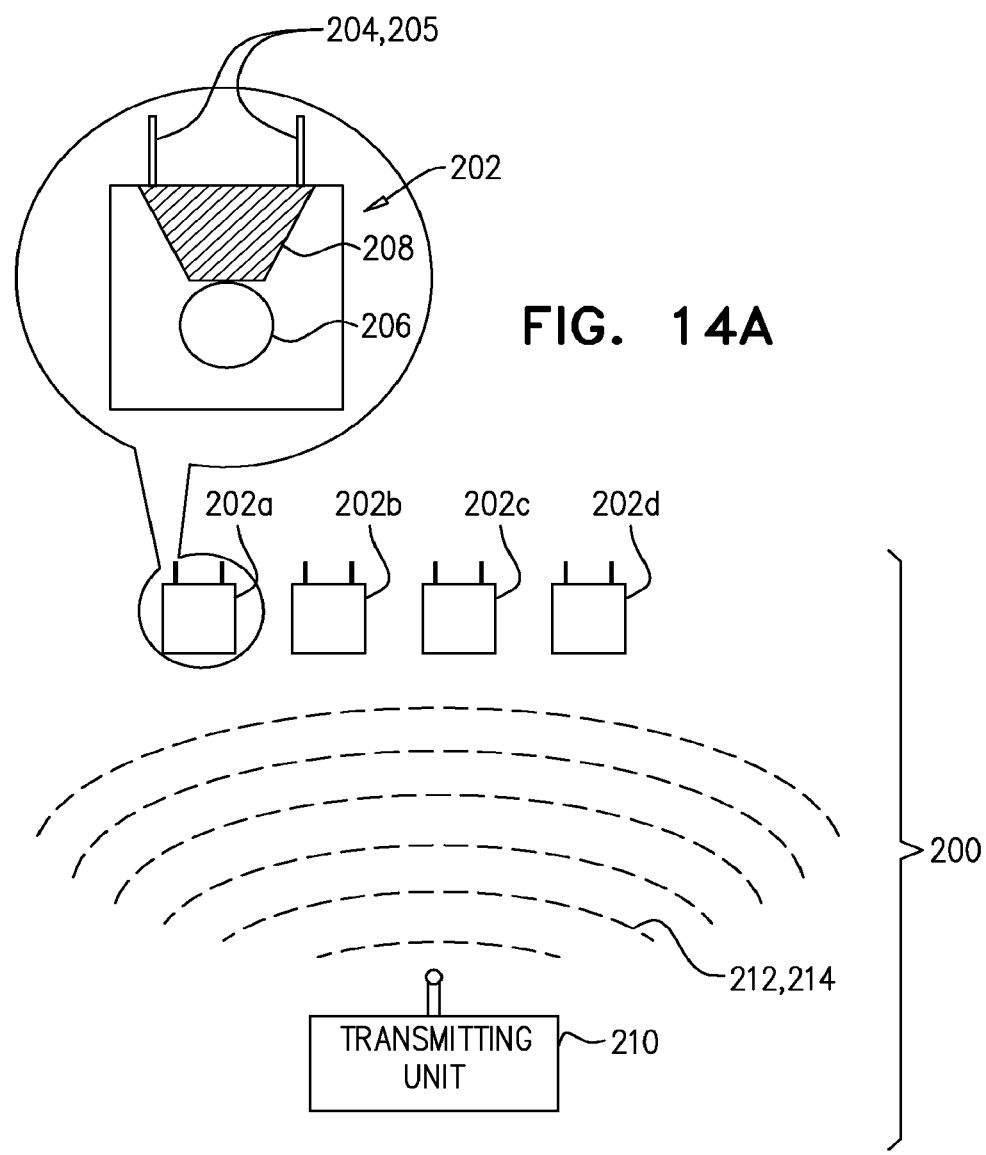

Reference is made to FIGS. 14A-C, which are schematic illustrations of a system 200 for applying a treatment to a tissue of a subject, in accordance with some applications of the invention. System 200 comprises a plurality of implants 202 (e.g., implants 202a, 202h, 202c and 202d), and a transmitting unit 210. Transmitting unit 210 transmits at least one wireless control signal 212, and each implant comprises one or more effector elements 204, which apply the treatment in response to control signal 212. That is, the each implant is "activated" in response to the control signal. System 200 is typically configured such that at least one of the implants applies the treatment asynchronously to at least another one of the implants. It is noted that in this patent application, including the specification and claims, "asynchronous" means "not starting at the same time," and does not necessarily indicate a lack of coordination and/or synchronization. For example, two implants that are configured such that one regularly applies treatment 100 ms after the other, may be synchronized, but apply the treatment asynchronously.

Transmitting unit 210 is typically extracorporeal. For example, the transmitting unit may be couplable to a part of the body of the subject, may be wearable by the subject, and/or may be disposed in an item of furniture on which the subject frequently rests, such as a bed or mattress.

Typically, each implant 202 comprises a receiver 206, configured to receive at least one of the wireless signals transmitted by transmitting unit 210, and a circuitry unit 208, which, at least in part responsively to the receiver receiving the wireless signal, drives effector elements 204 to apply the treatment. Typically, effector elements 204 comprise electrodes 205, and circuitry unit 208 drives a current via the electrodes, at least in part responsively to receiver 206 receiving signal 212. That is, the treatment typically comprises the delivery of the current.

FIG. 14B shows a technique by which system 200 may be configured such that at least one of the implants applies the treatment asynchronously to at least another one of the implants, in accordance with some applications of the invention. At least one of the implants 202 is configured to apply a treatment 216 after a duration (e.g., a delay) 218 following receiving signal 212 that is different from a duration following receiving the signal after which at least another one of the implants is configured to apply the treatment. For example, and as shown in FIG. 14B, transmitting unit 210 may be configured to transmit one control signal 212 (e.g., a pulse), all the implants (e.g., implants 202a, 202h, 202c, and 202d) receive the signal effectively simultaneously, and each implant is configured to apply the treatment after a respective different duration (e.g., durations 218a, 218b, 218c, and 218d, respectively) following receiving the signal.

Typically, duration 218 of each implant is pre-set (e.g., circuitry unit 208 of each implant is pre-configured thus). For some applications, the duration may be set and/or altered following implantation of implants 202, e.g., so as to optimize the application of the treatment. For example, duration 218 may be altered wirelessly by an operator, such as a physician who is monitoring the efficacy of the treatment. Alternatively or additionally, duration 218 may be automatically altered by system 200, using feedback from sensors that monitor the physiological changes caused by the treatment (not shown).

For the applications of the invention described with reference to FIG. 14B, the timing of the activation of the individual implants with respect to the timing of signal 212 is thereby coordinated predominantly by the implants themselves. Typically, the implants are activated sequentially, and the sequential activation may be described as an activation "wave." Thereby, for applications of the invention described with reference to FIG. 14B, the activation wave is initiated by control signal 212 from transmitting unit 210, but is internally coordinated predominantly by implants 202.

FIG. 14C shows another technique by which system 200 may be configured such that at least one of the implants applies the treatment asynchronously to at least another one of the implants, in accordance with some applications of the invention. Transmitting unit 210 is configured to transmit a plurality of control signals 212 (e.g., control signals 212a, 212b, 212c, and 212d), and to transmit at least one of the signals asynchronously to another one of the signals, and each implant is configured to receive a respective signal. For example, and as shown in FIG. 14C, transmitting unit 210 is configured to transmit each control signal 212 after a respective different duration (e.g., durations 218a, 218b, 218c, and 218d), and each implant, being configured to receive a respective control signal 212, applies treatment 216 while receiving the respective signal (e.g., effectively immediately upon receiving the respective signal).

For the applications of the invention described with reference to FIG. 14C, the timing of the activation of the individual implants is thereby coordinated predominantly by transmitting unit 210. For some applications, the implants are activated sequentially, and the sequential activation may be described as an activation "wave." Thereby, for applications of the invention described with reference to FIG. 14C, the activation wave is initiated and coordinated by transmitting unit 210. Alternatively, the implants are not activated sequentially. For example, the implants may be configured, implanted and/or controlled to treat independent tissues and/or conditions.

Each of the plurality of control signals (e.g., control signals 212a, 212b, 212c, and 212d) typically have an identifying feature that facilitates each implant to respond to a respective signals. That is, control signals 212a-d are typically "coded" (i.e., each signal includes a respective code), and each implant is configured to respond to a signal that includes a specific code. For example, implant 202a (e.g., circuitry unit 208 thereof) may be configured to drive a current through electrodes 205 in response to receiving control signal 212a, but not in response to any of control signals 212b, 212c, or 212d. For some applications, one or more of the implants are each configured to respond to more than one control signal, i.e., such that one signal activates more than one implant.

Reference is still made to FIGS. 14A-C. Typically, implants 202 do not comprise a power supply, such as a battery, that is able to continuously power the implants for a period greater than one minute (although the implants may comprise a temporary power storage element, such as a capacitor). Typically, transmitting unit 210 transmits at least one wireless power signal 214, and implants 202 are wirelessly powered by the power signal. For example, the power signal may comprise an electromagnetic signal, such as an RF signal, and each implant 202 comprises a rectifying antenna ("rectenna"). Alternatively or additionally, the power signal may comprise a magnetic signal, and the implants are powered by electromagnetic induction.

For some applications, power signal 214 is only transmitted at generally the same time as control signal(s) 212. For the applications of the invention described with reference to FIG. 14C, power is typically only transmitted generally at the same time as each control signal is transmitted (e.g. the power and control signals may comprise the same signal, such as a coded power signal).

For some applications of the invention, power signal 214 is transmitted at times when signals 212 are not transmitted. For example, power signal 214 may be transmitted both at generally the same time as control signal(s) 212, and at at least some times when signals 212 are not transmitted. For the applications of the invention described with reference to FIG. 14B, transmitting unit 210 typically begins to transmit power signal 214 generally at the same time as the unit transmits signal 212, and continues to transmit the power signal for a subsequent duration, such as until all implants 202 have responded to signal 212. That is, transmitting unit 210 typically transmits power signal 214 for a duration that is at least as long as duration 218d. Alternatively, transmitting unit 210 only transmits power signal 214 generally at the same time as control signal 212, and each implant comprises a temporary power storage element, such as a capacitor, capable of storing the power received from signal 214 until the implant applies the treatment (e.g., capable of storing the power for a respective duration 218).

For some applications, control signals 212 are modulated onto power signal 214 (e.g., by amplitude and/or frequency modulation). For example, with reference to FIG. 14C, power signal 214 may be transmitted for a duration which is at least as long as duration 218, and control signals 212a-d are modulated onto the power signal. For some applications, signals 212 and 214 may comprise the same signal (e.g., the power signal may be a coded power signal). For example, each implant may be configured to receive and/or be powered by a respective power signal having a respective characteristic, such as a respective frequency, and transmitting unit 210 is configured to activate each implant by transmitting the respective power signal.

For some applications, signals 212 and 214 comprise different signals. For example, the signals may be RF signals of different frequencies, or control signal 212 may be an RF signal whilst power signal 214 is a magnetic signal. For some applications, power signal 214 is not transmitted by transmitting unit 210. For example, power signal 214 may be provided by a separate power-transmitting unit (not shown). For some applications, implants 202 do comprise a power supply, such as a battery, that is able to continuously power the implants for a period greater than one minute. For such applications, implants 202 are typically wirelessly rechargeable.

Reference is still made to FIGS. 14A-C. Although system 200 is generally described as being typically configured to facilitate asynchronous application of the treatment by each implant, for some applications of the invention, system 200 is configured to facilitate generally independent control of each implant by the transmitting unit, which may include optionally driving two or more of the implants to apply the treatment simultaneously. For example, for some applications of the invention, transmitting unit 210 may be configured to drive a first activation "wave" in a first direction, by activating two electrodes at a time along the length of a stimulated tissue, and to subsequently drive a second activation wave in the opposite direction. Alternatively or additionally, one or more implants may be driven to apply the treatment for an extended duration, during which at least one other implant is activated and deactivated (e.g., repeatedly). It is to be noted that these examples are purely illustrative of independent implant control via wireless power transmission, and that the scope of the invention includes other sequences of implant activation.

Reference is made to FIG. 15, which is a schematic illustration of a system 220, for applying a treatment to sequential portions of a tubular anatomical structure 226 (e.g., a tubular organ) of a subject, in accordance with some applications of the invention. Structure 226 may comprise a hollow tubular structure such as a blood vessel or a part of the gastrointestinal tract (e.g., an intestine) of the subject, or may comprise a more solid tubular structure such as a nerve of the subject. System 220 comprises a plurality of implants 222 (e.g., implants 222a, 222b, 222c, and 222d), and transmitting unit 210. For some applications of the invention, system 220 and implants 222 are analogous to system 200 and implants 202, described hereinabove with reference to FIGS. 14A-C. Each implant 222 comprises one or more effector elements 224, which apply a treatment in response to control signal 212, transmitted by transmitting unit 210. System 220 is configured such that at least one of the implants applies the treatment asynchronously to at least another one of the implants.

Typically, system 220 is configured such that each implant 222 is implanted at a pre-selected distance from at least another implant. Typically, system 220 comprises a support 228 that is configured to facilitate such implantation, e.g., to facilitate simultaneous delivery of all the implants and/or to retain the implants 222 at a pre-selected spacing. FIG. 15 shows structure 226 comprising a hollow tubular structure of the subject, and support 228 comprising a stent to which implants 222 are coupled, and which is typically transluminally delivered to the lumen of the structure. Alternatively, structure 226 may comprise a nerve, and support 228 comprises a nerve cuff that is disposable around the nerve. Further alternatively, support 228 may comprise a removable support, such as part of a delivery device, e.g., that is decoupled from implants 222 following implantation of the implants. Further alternatively, support 228 may comprise any implantable medical device, such as an orthopedic device (e.g., a bone screw), or a device configured to be placed near the spinal cord.

Effector elements 224 typically comprise electrodes 205. Implants 222 are implanted such that electrodes 205 are in electrical contact with structure 226 (e.g., disposed against the structure). For example, support 228 is pressed against the structure. For some applications, electrodes 205 comprise ring electrodes, and implants 222 are coupled to structure 226 such that the ring electrodes are disposed over a portion of the structure. Each implant 222 applies the treatment at the portion of structure 226 to which it is coupled, by driving a current via electrodes 205, into the portion of the structure. For some applications, when structure 226 comprises a nerve, the current is configured to induce at least one action potential in the nerve. For some applications, when structure 226 comprises a hollow tubular structure, such as a blood vessel or intestine, the current is configured to induce constriction in at least the portion of structure 226 to which the electrode is in contact.

For some applications, when structure 226 comprises a hollow tubular structure, effector element 224 comprises an annular constricting element that is couplable to a respective portion of the structure, and circuitry unit 208 of implant 222 is configured to drive the constricting element to constrict, thereby inducing constriction of the portion of the structure.

For some applications of the invention, system 220 is configured such that at least one of the implants applies the treatment asynchronously to at least another one of the implants, using techniques described with reference to FIG. 14B, mutatis mutandis. For example, transmitting unit 210 may be configured to transmit one control signal 212, all the implants (e.g., implants 222a, 222b, 222c, and 222d) receive the signal effectively simultaneously, and each implant is configured to apply the treatment after a different (e.g., pre-set) duration following receiving the signal.

For some applications of the invention, system 220 is configured such that at least one of the implants applies the treatment asynchronously to at least another one of the implants, using techniques described with reference to FIG. 14C, mutatis mutandis. For example, transmitting unit 210 may be configured to transmit a plurality of control signals 212, and to transmit at least one of the control signals asynchronously to another one of the control signals, and each implant is configured to receive a respective control signal and to responsively (e.g., immediately) apply the treatment in the portion of structure 226 to which it are coupled.

When system 220 is configured to induce constriction in portions of a tubular anatomical structure such as a blood vessel or intestine, system 220 is typically configured to induce pumping in the structure. Typically, system 220 is configured this way by being configured such that implants 222 induce constriction (i.e., are activated) consecutively according to the order in which they are disposed on structure 226, thereby inducing an advanced form of peristaltic pumping. For example, consecutive activation of implants 222a, 222b, 222c, and 222d may induce peristalsis in structure 226.

For some applications of the invention, structure 226 comprises a blood vessel of the subject, and system 220 is used to alter blood flow in the blood vessel. For example, structure 226 may comprise the aorta of the subject, and system 220 may be used to enhance downstream bloodflow in the aorta by inducing downstream peristalsis (e.g., to treat peripheral vascular disease) and/or to increase blood flow into the coronary arteries by inducing upstream peristalsis (e.g., during ventricular diastole).

For some applications of the invention, structure 226 is a component of the gastrointestinal tract, such as an intestine or an esophagus, and system 220 may be used to induce peristalsis or tighten a sphincter or valve in the component of the gastrointestinal tract. For example, system 220 may be used to induce peristalsis in an esophagus of the subject or tighten the lower esophageal sphincter, so as to treat gastroesophageal reflux disease. Alternatively or additionally, system 220 may be used to induce peristalsis in a duodenum of the subject, so as to treat obesity.

For some applications of the invention, pumping is induced by stimulating one or more skeletal muscles in a vicinity of a blood vessel, e.g., so as to compress the blood vessel. Typically, such pumping is induced by stimulating two or more skeletal muscles to contract. For some such applications of the invention, system 200 is used, rather than system 220.

Reference is still made to FIGS. 14A-15. As described hereinabove, systems 200 and 220 are configured such that at least implant applies the treatment asynchronously to at least another implant. Typically, the systems are thus configured by being configured such that a state of at least one of the implants changes asynchronously to the state of at least another one of the implants. For example, the implants may each have an "activated" state, in which the treatment is applied and/or constriction is induced, and an "off" state, in which that treatment is not applied and/or constriction is not induced. For some applications of the invention, the implants may have one or more other states, such as a "ready" state, and be configured to enter the "ready" state in response to one or more signals from the transmitting unit. For example (see FIG. 14C), when transmitting unit 210 transmits control signal 212a, and implant 202a responsively applies the treatment (i.e., enters the "activated" state thereof), implant 202b may be configured to enter the "ready" state thereof (e.g., to charge a capacitor thereof) in response to control signal 212a, thereby becoming ready to apply the treatment when control signal 212b is received. It is hypothesized that such configuration reduces a response time of each implant to the control signal.

Figure 16:
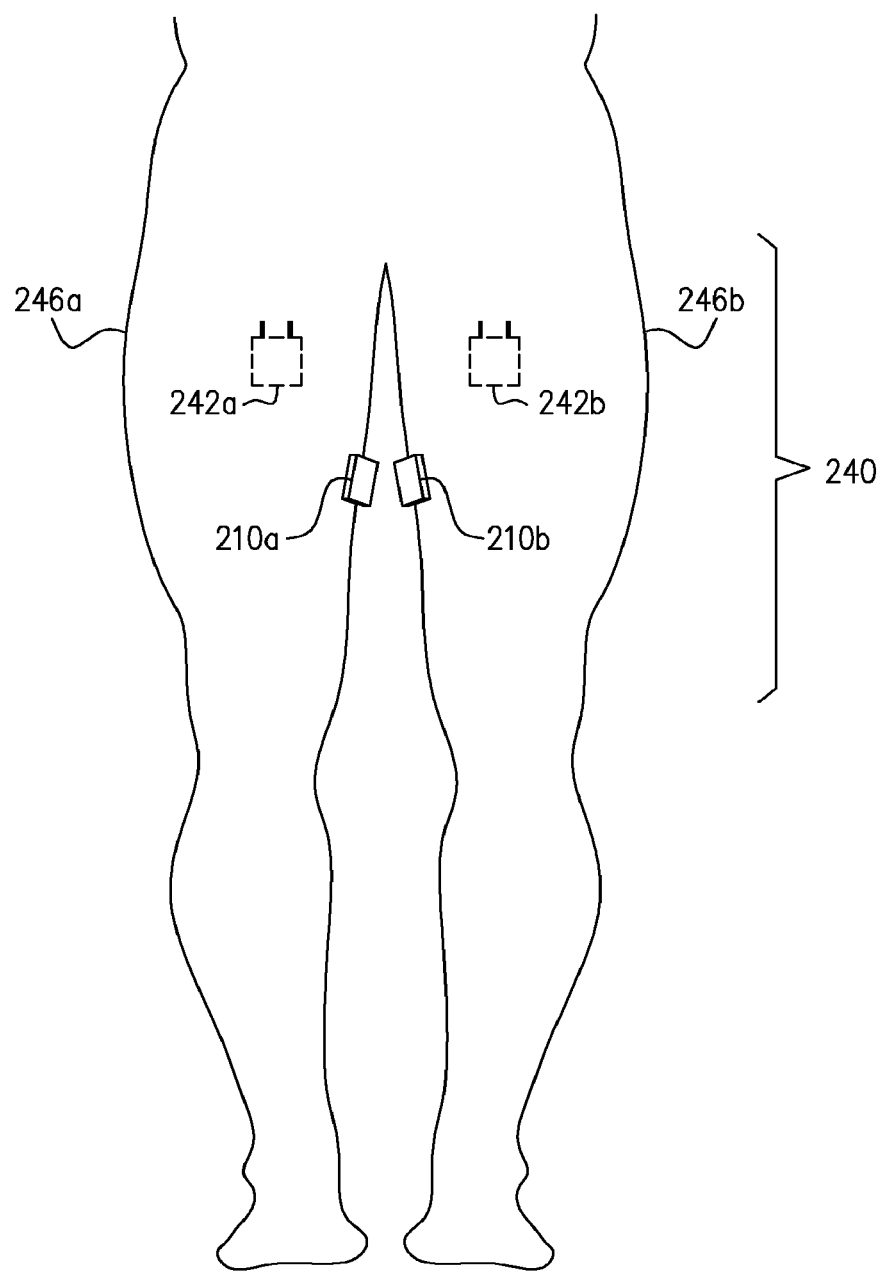
FIG. 16 is a schematic illustration of a system for asynchronous application of treatment using a plurality of implants, in accordance with some applications of the invention.

Reference is made to FIG. 16, which is a schematic illustration of a system 240, for applying a treatment to a plurality of tissues of a subject, in accordance with some applications of the invention. System 240 comprises a plurality of implants 242 (e.g., implants 242a and 242b), and one or more transmitting units 210 (e.g., transmitting units 210a and 210b). For some applications of the invention, implants 242a and 242b are similar to each other and are configured to apply similar treatments, e.g., to bilateral tissues, such as opposing limbs, such as legs 246 (e.g., leg 246a and 246b) of the subject. For some applications, implants 242 are implanted, and configured, to treat neuropathic leg pain. Alternatively, implants 242a and 242b are configured to treat different conditions and/or to apply different treatments.

Typically, transmitting units 210a and 210b and/or implants 242a and 242b are disposed, at least some of the time, in close proximity to each other (e.g., within 1 m of each other, such as within 30 cm of each other, such as within 10 cm of each other). For example, and as shown in FIG. 16, a first transmitting unit 210a is coupled (e.g., adhered and/or strapped) to a first leg of a subject, and intended (e.g., configured) to power and control a first implant 242a, and a second transmitting unit 210b is coupled to a second leg of the subject, and intended (e.g., configured) to control a second implant 242b.

The use of one or more transmitting units to control a plurality of implants may be subjected to problems, such as interference and/or misdirected signals. That is, a first implant may receive, and respond to, a signal that is intended to be received by a second implant. This is more likely when the transmitting units and implants are in close proximity to each other. For example, implant 242b might respond to signals transmitted by unit 210a, and/or implant 242a might respond to signals transmitted by unit 210b.

Typically, apparatus 240 is configured to use coded signals, e.g., as described hereinabove with reference to FIGS. 14A-15. For example, transmitting unit 210a may be configured to transmit wireless power at a first frequency, which implant 242a is configured to receive and/or by which implant 242a is configured be powered; while transmitting unit 210b is configured to transmit wireless power at a second frequency, which implant 242b is configured to receive and/or by which implant 242b is configured to be powered. Alternatively or additionally, first and second pulse widths may be used to "code" the signals. Alternatively or additionally, first and second on-off patterns (i.e., durations for which the wireless power is transmitted and not transmitted) may be used to "code" the signals. It is hypothesized that the use of coded signals reduces (e.g., prevents) misdirected signals when wirelessly controlling a plurality of implants, and especially implants that are in close proximity. Such misdirected signals may interfere with treatment and/or cause the subject discomfort and/or pain.

For some applications of the invention, transmitting units 210a and 210b are configured to be in wireless communication with each other. For example, it may be desirable for the transmitting units to coordinate the driving of implant 242b with respect to the driving of implant 242a. For example, transmitting unit 210b may be configured to drive implant 242b only when transmitting unit 210a is not driving implant 242a (i.e., asynchronously). Alternatively, transmitting unit 210b may be configured to drive implant 242b at the same time as transmitting unit 210a drives implant 242a. It is to be noted that these two examples are illustrative, and that the scope of the invention includes any coordination between transmitting units 210a and 210b for driving implants 242a and 242b.

Reference is again made to FIGS. 14A-16. For some applications of the invention, asynchronous application of treatment comprises coordinated application of treatment. For example, the system may be configured to provide a "wave" of stimulation, such as to induce peristalsis (e.g., as described with reference to FIG. 15). Alternatively, for some applications of the invention, asynchronous application of treatment comprises independent application of one or more treatments. For example, the system may be configured to provide two different and independent treatments using two different implants that are controlled by the same transmitting unit. It is to be noted that the techniques for controlling multiple implants, described with reference to FIGS. 14A-16 may be combined with other techniques and other implants, such as those described with reference to FIGS. 1-13, mutatis mutandis.

Figure 17A:
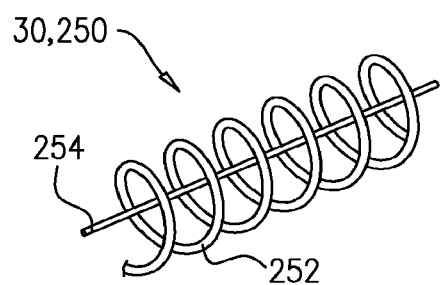
FIGS. 17A-E are schematic illustrations of an antenna for use with systems for wireless neurostimulation, in accordance with respective applications of the invention.
Figure 17B:
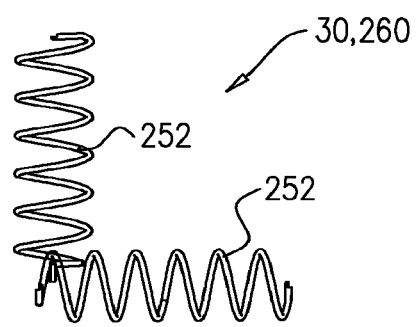
Figure 17C:
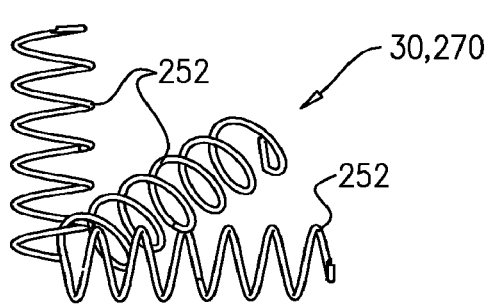

Reference is made to FIGS. 17A-E, which are schematic illustrations of antenna 30, in accordance with respective applications of the invention. Hereinabove, antenna 30 is illustrated as a coiled antenna purely as an example. Further, non-limiting examples of embodiments of antenna 30, for use with one or more of the implants described hereinabove, are described with reference to FIGS. 17A-E. FIG. 17A shows antenna 30, comprising an antenna 250, which comprises a coil 252 disposed around a ferrite core 254. FIG. 17B shows antenna 30 comprising an antenna 260, which comprises two mutually-perpendicular coils 252. FIG. 17C shows antenna 30 comprising an antenna 270, which comprises three mutually-perpendicular coils 252. It is hypothesized that mutually-perpendicular coils facilitate reception of wireless power and/or other signals, e.g., independently of an orientation of the implant. For some applications, antenna 260 and/or antenna 270 comprise at least one ferrite core 254, as described with reference to FIG. 17A, mutatis mutandis. For example, each coil 252 of antenna 260 and/or 270 may be disposed around a ferrite core 2M.

Figure 17D:
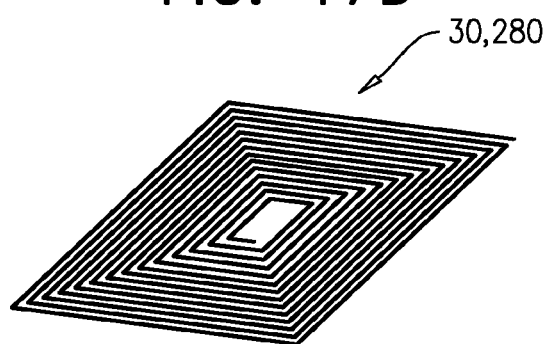

FIG. 17D shows antenna 30 comprising a planar spiral antenna 280. Antenna 280 is shown as a square spiral, but may be a round spiral, or any other spiral.

Figure 17E:
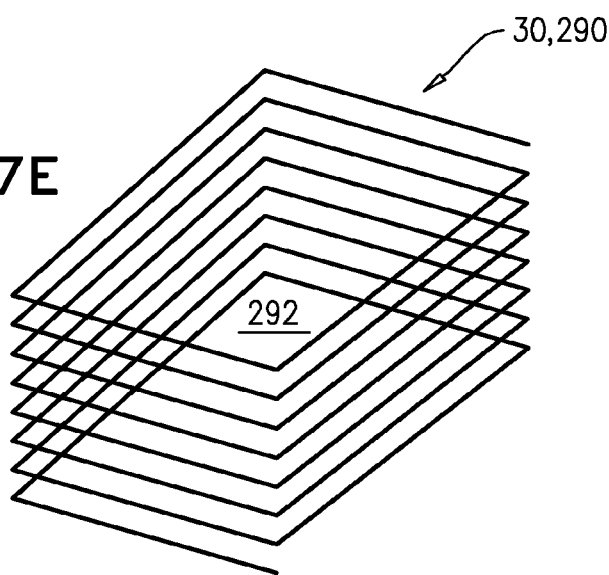

FIG. 17E shows antenna 30 comprising a helical antenna 290. Antenna 290 is shown as a cuboid helix, but may be a cylindrical helix, or any other helix. It is hypothesized that a helical antenna facilitates economization of space, by other components (e.g., circuitry units 22 and/or 208) being disposable within a void 292, defined by the helix of the antenna.

Reference is again made to FIGS. 1-17E. For some applications of the invention, the implants described hereinabove may comprise effector elements other than electrodes (e.g., the effector elements described hereinabove may comprise other components, and/or the electrodes described hereinabove may be replaced with other effector elements). For example, for some applications of the invention, one or more of the effector elements may comprise a vibrating element, and the treatment is applied by the circuitry unit driving the vibrating element to vibrate. This vibrating element may be employed in addition to or instead of any or all of the electrodes (e.g., electrodes 28) described herein, with reference to FIGS. 1-17E. It is hypothesized that, for some applications, vibrational stimulation is useful for stimulating sensory fibers. For example, an implant, implanted subcutaneously as described with reference to FIG. 13, may be used to vibrationally stimulate sensory fibers in the skin of the subject.

For some applications, a combination of electrodes and vibrating units is used in the same implant and/or in different implants. It is noted with reference to FIGS. 11 and 12 that insulating member 136 may be mechanically insulating in order to reduce passage of vibrations into deeper tissues, and to instead maintain more of the vibrational energy near the sensory fibers in the skin of the subject. For such applications, this mechanically-insulating member typically acts as an inhibiting element that inhibits direct stimulation of one or more deeper nerves.

Similarly, one or more of the effector elements described hereinabove may comprise a heating and/or cooling element, a pressure-exerting element, an ultrasound transducer, and/or a laser. Alternatively or additionally, one or more of the implants described hereinabove may comprise one or more sensors, e.g., to provide feedback.

The implantation sites and disorders described hereinabove are examples for illustrating the use of the techniques described herein. The implants described herein may be implanted at a variety of implantation sites, and the techniques described herein may be used to treat a variety of disorders. For example:

stimulation of the tibial nerve (and/or of sensory fibers that lead to the tibial nerve), e.g., to treat neuropathic pain and/or urge incontinence;

stimulation of sensory fibers that lead to the radial and/or ulnar nerves, e.g., to treat tremor (e.g., essential tremor, and tremor associated with Parkinson's disease);

stimulation of the occipital nerve, e.g., to treat migraine;

stimulation of the sphenopalatine ganglion, e.g., to treat cluster headaches;

stimulation of the sacral and/or pudendal nerve, e.g., to treat urge incontinence;

direct stimulation of an implantation site within the brain (e.g., deep brain stimulation), such as the thalamus, e.g., to treat tremor, obsessive-compulsive disorder, and/or depression;

stimulation of the vagus nerve, e.g., to treat epilepsy, depression, inflammation, tinnitus, and/or congestive heart failure (e.g., by incorporating some or all of device 20 into an aortic stent);

stimulation of baroreceptors in a blood vessel wall (e.g., the wall of the carotid sinus and/or aorta, e.g., to treat high blood pressure);

stimulation of the spinal cord, e.g., to treat pain;

stimulation of one or more muscles (such as shoulder muscles), e.g., to treat muscle pain;

stimulation of the medial nerve, e.g., to treat carpal tunnel syndrome;

stimulation of the hypoglossal nerve and/or one or more muscles of the tongue, e.g., to treat obstructive sleep apnea;

stimulation of cardiac tissue, e.g., to pace and/or defibrillate the heart (e.g., the use of the implant as a leadless pacemaker);

stimulation to treat dystonia;

stimulation of the vagus nerve, e.g., to treat epilepsy;

stimulation to treat interstitial cystitis;

stimulation to treat gastroparesis;

stimulation to treat obesity;

stimulation of the anal sphincter, e.g., to treat fecal incontinence;

stimulation to treat bowel disorders;

stimulation of peripheral nerves of the spinal cord, e.g., to treat chronic pain;

stimulation of the dorsal root ganglion for the treatment of chronic pain; and stimulation of motor nerves and/or muscles to improve mobility.

Implants whose effector element comprises an electrode and/or a vibrating element may also be used to block nerve signals, such as to induce local anesthesia. It is hypothesized that paresthesia may be induced by driving a relatively low-frequency current (e.g., greater than 1 and/or less than 120 Hz, e.g., between 10 and 40 Hz) into the nerve, and that a relatively high-frequency current (e.g., greater than 5 and/or less than 20 kHz, e.g., between 10 and 20 kHz) may be used to induce complete blocking.

Tibial nerve stimulation (e.g., electrical stimulation) may be used to treat pain, such as neuropathic pain, e.g., neuropathic pain in the legs of a subject. Implants, such as those described hereinabove, may be used to provide such stimulation. However, variation between subjects exists, and such treatment does not sufficiently reduce pain in all subjects. In experiments conducted by the inventors, percutaneous electrodes (i.e., temporary electrodes) were used to stimulate the tibial nerve of 8 subjects by percutaneously delivering at least part (e.g., a tip) of the electrodes to a site in a vicinity of the tibial nerve, and applying a current to the tibial nerve. Sessions comprised 15-60 minutes of stimulation. Of these 8 subjects, 6 experienced good pain relief and 2 experienced moderate pain relief. Interestingly, the degree of pain relief for each subject in the first session was similar to that for the successive sessions. That is, a first session of stimulation was indicative of responsiveness to subsequent treatment. It is therefore hypothesized that data from a single session of percutaneous stimulation of the tibial nerve, lasting 1-120 minutes (e.g., 10-30 minutes) of stimulation and successfully inducing paresthesia in the subject's foot, may be used to facilitate a decision of whether to implant one or more stimulatory implants at the tibial nerve of a given subject.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus configured for use with tissue of a subject, the apparatus comprising a neurostimulator implant, the implant comprising:
   an insulating member having a first side and a second side; and
   an elongate circuitry unit:
      (a) having a first end portion and a second end portion, and defining a longitudinal axis therebetween,
      (b) comprising:
         a first electrode, disposed on an outer surface of the circuitry unit at the first end portion;
         a second electrode, disposed on the outer surface of the circuitry unit at the second end portion; and
         circuitry, disposed inside the circuitry unit, and configured to be wirelessly powered to drive an electrical current between the first and second electrodes, and
      (c) coupled to a medial part of the insulating member, such that:
         the circuitry unit is disposed alongside the medial part of the insulating member, on the first side of the insulating member, bulging away from insulating member to define a generally arced portion of the implant, and is configured to facilitate conduction of the electrical current in a first direction away from the generally arced portion of the implant,
         lateral parts of the insulating member extend laterally outward from the medial part to define lateral zones extending laterally beyond edges of the circuitry unit, wherein there are no electrodes of the implant disposed in the lateral zones, and
         the second side of the insulating member defines a generally flat side of the implant, facing a second direction opposite the first direction and away from the generally arced portion of the implant and the first and second electrodes of the circuitry unit.

2. The apparatus according to claim 1, wherein the first electrode is disposed on the outer surface of the circuitry unit such that the first electrode extends around the arced portion of the implant at the first end portion, and the second electrode is disposed on the outer surface of the circuitry unit such that the second electrode extends around the arced portion of the implant at the second end portion.

3. The apparatus according to claim 1, wherein the insulating member comprises insulating silicone.

4. The apparatus according to claim 1, wherein the insulating member inhibits conduction of the electrical current away from the implant in the second direction.

5. The apparatus according to claim 1, wherein the implant is configured to be implanted in a limb of the subject.

6. The apparatus according to claim 1, wherein the circuitry is configured to configure the electrical current to have a frequency of 10-40 Hz.

7. The apparatus according to claim 1, wherein (a) the implant does not comprise a power supply, or (b) the implant comprises a power supply that is not able to continuously power the implant for a period greater than one minute.

8. The apparatus according to claim 1, wherein the implant is configured such that the driving of the electrical current does not induce contraction of a muscle of the subject.

9. The apparatus according to claim 1, wherein the circuitry is configured to configure the electrical current to stimulate a tibial nerve.

10. The apparatus according to claim 9, wherein the circuitry is configured to configure the electrical current to induce paresthesia.

11. The apparatus according to claim 9, wherein the circuitry is configured to configure the electrical current to treat neuropathic pain.

12. The apparatus according to claim 1, wherein the circuitry unit has a length, from a first end thereof to a second end thereof, of 5-50 mm.

13. The apparatus according to claim 12, wherein the length of the circuitry unit is 10-30 mm.

14. The apparatus according to claim 12, wherein the circuitry unit is 1-5 mm in width.

15. The apparatus according to claim 14, wherein the circuitry unit is 1.5-3 mm in width.

16. The apparatus according to claim 1, wherein each of the lateral zones extends greater than 1 mm laterally beyond the circuitry unit.

17. The apparatus according to claim 16, wherein each of the lateral zones extends greater than 2 mm laterally beyond the circuitry unit.

18. The apparatus according to claim 17, wherein each of the lateral zones extends greater than 5 mm laterally beyond the circuitry unit.

19. The apparatus according to claim 1, further comprising a transmitting unit, configured to transmit wireless power, and wherein the circuitry is configured to be wirelessly powered, by the wireless power, to drive the electrical current between the first and second electrodes.

20. The apparatus according to claim 19, wherein the transmitting unit is configured to be wearable by the subject.

21. The apparatus according to claim 19, wherein the circuitry is configured to apply the electrical current only when the implant receives the wireless power.

* * * * *